(12) United States Patent
Doubet et al.

(10) Patent No.: US 11,707,579 B2
(45) Date of Patent: Jul. 25, 2023

(54) SYRINGE ADAPTER FOR MEDICATION

(71) Applicants: James T. Doubet, Parker, CO (US); Paul D. Doubet, Farmington, IL (US)

(72) Inventors: James T. Doubet, Parker, CO (US); Paul D. Doubet, Farmington, IL (US)

( * ) Notice: Subject to any disclaimer, the term of this patent is extended or adjusted under 35 U.S.C. 154(b) by 92 days.

(21) Appl. No.: 17/355,452

(22) Filed: Jun. 23, 2021

(65) Prior Publication Data
US 2021/0316084 A1 Oct. 14, 2021

Related U.S. Application Data

(60) Continuation of application No. 16/895,370, filed on Jun. 8, 2020, now Pat. No. 11,071,834, which is a
(Continued)

(51) Int. Cl.
*A61M 5/32* (2006.01)
*A61M 5/34* (2006.01)
(Continued)

(52) U.S. Cl.
CPC .......... *A61M 5/3293* (2013.01); *A61J 1/2096* (2013.01); *A61M 5/1782* (2013.01);
(Continued)

(58) Field of Classification Search
CPC .......... A61M 2039/1077; A61M 5/345; A61M 5/3293; A61M 5/1782; A61M 5/347
See application file for complete search history.

(56) References Cited

U.S. PATENT DOCUMENTS

| 822,079 A | 5/1906 | Roussy |
| 2,626,603 A | 1/1953 | Gabriel |

(Continued)

FOREIGN PATENT DOCUMENTS

| EP | 1923086 B1 | 4/2012 |
| KR | 20120107161 A | 10/2012 |

(Continued)

OTHER PUBLICATIONS

In re James T. Doubet, et al., U.S. Appl. No. 17/404,954, filed Aug. 17, 2021, Office Action, dated Nov. 9, 2021, 39 pages.
(Continued)

*Primary Examiner* — Theodore J Stigell
*Assistant Examiner* — Rachel T. Smith
(74) *Attorney, Agent, or Firm* — Marcia L. Doubet

(57) ABSTRACT

Improved apparatus for use with medication in fluid form, which is particularly beneficial for medications having a relatively high viscosity. The disclosed syringe adapter has an opening that is relatively large, as compared to a conventional needle, and thus affixing the disclosed syringe adapter to a syringe improves syringeability of higher-viscosity medications. Some embodiments feature a lateral extension that prevents inserting the syringe adapter too far into a medicine bottle, and some embodiments feature a component that assists in firmly grasping. When the disclosed syringe adapter is affixed to a pistol-grip or tab-handled syringe, the medication withdrawn into the pistol-grip syringe can be more easily administered from the syringe barrel. In some embodiments, the syringe adapter will be replaced with a needle prior to injecting the medication, while in some other embodiments, the needle is affixed to the in-place syringe adapter for the injection. In yet other embodiments, the needle is affixed to a needle holder that, in turn, is affixed to the in-place syringe adapter for the injection.

20 Claims, 18 Drawing Sheets

Related U.S. Application Data division of application No. 16/698,471, filed on Nov. 27, 2019, now Pat. No. 10,709,850, which is a continuation-in-part of application No. 16/203,858, filed on Nov. 29, 2018, now Pat. No. 11,090,444, which is a continuation-in-part of application No. 16/166,111, filed on Oct. 21, 2018, now Pat. No. 11,097,058, which is a continuation-in-part of application No. 16/010,155, filed on Jun. 15, 2018, now Pat. No. 11,337,894, application No. 17/355,452 is a continuation of application No. 16/895,370, filed on Jun. 8, 2020, now Pat. No. 11,071,834, which is a division of application No. 16/698,471, filed on Nov. 27, 2019, now Pat. No. 10,709,850, which is a continuation-in-part of application No. 16/563,896, filed on Sep. 8, 2019, now abandoned, which is a continuation-in-part of application No. 16/166,111, filed on Oct. 21, 2018, now Pat. No. 11,097,058, which is a continuation-in-part of application No. 16/010,155, filed on Jun. 15, 2018, now Pat. No. 11,337,894.

(51) Int. Cl.
*A61J 1/20* (2006.01)
*A61M 5/178* (2006.01)
*A61M 5/31* (2006.01)
*A61M 39/10* (2006.01)

(52) U.S. Cl.
CPC .............. *A61M 5/347* (2013.01); *A61M 5/34* (2013.01); *A61M 2005/3114* (2013.01); *A61M 2039/1077* (2013.01)

(56) References Cited

U.S. PATENT DOCUMENTS

| | | |
|---|---|---|
| 2,752,919 A | 7/1956 | Gabriel |
| 3,320,954 A | 5/1967 | Cowley |
| 3,436,828 A | 4/1969 | Dragan |
| 3,958,570 A | 5/1976 | Vogelman et al. |
| 4,046,145 A | 9/1977 | Choksi et al. |
| 4,294,250 A | 10/1981 | Dennehey |
| 4,316,462 A | 2/1982 | Baker |
| 4,338,925 A | 7/1982 | Miller |
| 4,472,141 A | 9/1984 | Dragan |
| 4,664,655 A | 5/1987 | Orentreich et al. |
| 4,758,158 A | 7/1988 | Pierce et al. |
| 4,758,234 A | 7/1988 | Orentreich et al. |
| 4,927,417 A | 5/1990 | Moncada et al. |
| 5,047,021 A | 9/1991 | Utterberg |
| 5,195,985 A | 3/1993 | Hall |
| 5,322,510 A | 6/1994 | Lindner et al. |
| 5,445,523 A | 8/1995 | Fischer et al. |
| 5,509,911 A | 4/1996 | Cottone, Sr. et al. |
| 5,733,258 A | 3/1998 | Lane |
| 5,746,733 A | 5/1998 | Capaccio et al. |
| 6,117,113 A | 9/2000 | Novacek et al. |
| 6,511,472 B1 | 1/2003 | Hayman et al. |
| 6,787,568 B1 | 9/2004 | Mihalik |
| 6,790,867 B2 | 9/2004 | Kohan et al. |
| 6,981,618 B2 | 1/2006 | Reisinger |
| 7,347,458 B2 | 3/2008 | Rome et al. |
| 7,472,932 B2 | 1/2009 | Weber et al. |
| 7,682,343 B2 | 3/2010 | Westbye |
| 7,699,609 B2 | 4/2010 | Lawter et al. |
| 7,803,139 B2 | 9/2010 | Fangrove, Jr. |
| 8,034,845 B2 | 10/2011 | Freehauf et al. |
| 8,044,102 B2 | 10/2011 | Kohan et al. |
| D736,915 S | 8/2015 | Schultz |
| 9,295,788 B2 | 3/2016 | Green |
| 9,801,788 B2 | 10/2017 | Banik et al. |
| 10,709,850 B2 | 7/2020 | Doubet et al. |
| 11,071,834 B2 | 7/2021 | Doubet et al. |
| 11,090,444 B2 | 8/2021 | Doubet et al. |
| 11,097,058 B2 | 8/2021 | Doubet et al. |
| 11,173,257 B2 | 11/2021 | Doubet |
| 2002/0173753 A1 | 11/2002 | Caizza et al. |
| 2003/0236501 A1 | 12/2003 | Donnan et al. |
| 2004/0039365 A1 | 2/2004 | Aramata et al. |
| 2004/0068266 A1 | 4/2004 | Delmotte |
| 2004/0116873 A1 | 6/2004 | Fojtik |
| 2005/0054979 A1* | 3/2005 | Liu .............. A61M 5/3243 604/110 |
| 2006/0047251 A1 | 3/2006 | Bickford Smith et al. |
| 2006/0270996 A1 | 11/2006 | Fojtik |
| 2006/0271015 A1 | 11/2006 | Mantell |
| 2007/0060898 A1 | 3/2007 | Shaughnessy et al. |
| 2007/0183986 A1 | 8/2007 | Allred et al. |
| 2007/0203451 A1 | 8/2007 | Murakami et al. |
| 2008/0015539 A1 | 1/2008 | Pieroni et al. |
| 2008/0115796 A1 | 5/2008 | Montanari et al. |
| 2008/0188816 A1 | 8/2008 | Shimazaki et al. |
| 2008/0287884 A1 | 11/2008 | Warden et al. |
| 2009/0182284 A1 | 7/2009 | Morgan |
| 2009/0227894 A1 | 9/2009 | Fojtik |
| 2011/0028909 A1 | 2/2011 | Lum et al. |
| 2012/0130317 A1 | 5/2012 | Thorley |
| 2012/0184938 A1 | 7/2012 | Lev et al. |
| 2012/0265163 A1 | 10/2012 | Cheng et al. |
| 2013/0018354 A1 | 1/2013 | Sund et al. |
| 2013/0178806 A1 | 7/2013 | Felix-Faure et al. |
| 2013/0331810 A1 | 12/2013 | Bazala et al. |
| 2014/0066840 A1 | 3/2014 | Mantell |
| 2014/0261860 A1 | 9/2014 | Heath et al. |
| 2017/0165192 A1 | 6/2017 | Georges et al. |
| 2017/0203086 A1 | 7/2017 | Davis |
| 2018/0050183 A1 | 2/2018 | Taylor |
| 2018/0104150 A1 | 4/2018 | Dubaele et al. |
| 2018/0344570 A1 | 12/2018 | Davis et al. |

FOREIGN PATENT DOCUMENTS

| | | |
|---|---|---|
| KR | 10-2047319 B1 | 11/2019 |
| WO | WO2004/096326 A1 | 11/2004 |
| WO | 2012/023955 A1 | 2/2012 |
| WO | 2014145959 A1 | 9/2014 |
| WO | 2017/091643 A1 | 6/2017 |

OTHER PUBLICATIONS

In re James T. Doubet, et al., U.S. Appl. No. 17/404,954, filed Aug. 17, 2021, Office Action, dated Feb. 25, 2022, 27 pages.
PCT Application PCT/US2019/062926, International Search Report dated Feb. 12, 2020 (2 pages).
PCT Application PCT/US2019/062926, Written Opinion of the International Searching Authority dated Feb. 12, 2020 (6 pages).
PCT Application PCT/US2019/056282, International Search Report dated Jan. 7, 2020 (2 pages).
PCT Application PCT/US2019/056282, Written Opinion of the International Searching Authority dated Jan. 7, 2020 (5 pages).
PCT Application PCT/US2020/061523, International Preliminary Report on Patentability dated Jun. 9, 2022 (10 pages).
In re James T. Doubet, et al., U.S. Appl. No. 16/563,896, filed Sep. 8, 2019, Office Action, dated Jan. 14, 2021, 22 pages.
In re James T. Doubet, et al., U.S. Appl. No. 16/203,858, filed Nov. 29, 2018, Office Action, dated Nov. 21, 2021, 17 pages.
In re James T. Doubet, et al., U.S. Appl. No. 16/166,111, filed Oct. 21, 2018, Office Action, dated Nov. 11, 2021, 22 pages.
PCT Application PCT/US2019/036774, International Preliminary Report on Patentability dated Dec. 15, 2020 (6 pages).
PCT Application PCT/US2020/061523, International Search Report dated Feb. 9, 2021 (3 pages).
PCT Application PCT/US2020/061523, Written Opinion of the International Searching Authority dated Feb. 9, 2021 (8 pages).
PCT Application PCT/US2020/048978, International Search Report dated Nov. 10, 2020 (2 pages).
PCT Application PCT/US2020/048978, Written Opinion of the International Searching Authority dated Nov. 10, 2020 (6 pages).

(56) References Cited

OTHER PUBLICATIONS

In re James T. Doubet, et al., U.S. Appl. No. 16/895,370, filed Jun. 8, 2020, Office Action, dated Dec. 8, 2021, 22 pages.
In re James T. Doubet, et al., U.S. Appl. No. 16/563,896, filed Sep. 8, 2019, Office Action, dated May 18, 2021, 25 pages.
In re James T. Doubet, et al., U.S. Appl. No. 16/563,896, filed Sep. 8, 2019, Advisory Action, dated Jun. 21, 2021, 3 pages.
Colomer, S., et al., "Syringeability and Viscosity Comparative of Different Florfenicol Formulations", publication date unknown, printed from http://marketing.hipra.com/SELECTNEWS/trials/Syringeabiliy_viscosity_comparative_of_FLORFENICOL_formulations.pdf on May 14, 2018. 1 page.
In re James T. Doubet, et al., U.S. Appl. No. 16/166,111, filed Oct. 21, 2018, Office Action, dated Apr. 3, 2020, 21 pages.
In re James T. Doubet, et al., U.S. Appl. No. 16/203,858, filed Nov. 29, 2018, Office Action, dated Apr. 3, 2020, 22 pages.
In re James T. Doubet, et al., U.S. Appl. No. 16/895,370, filed Jun. 8, 2020, Office Action, dated Oct. 15, 2020, 25 pages.
"(Revised) List of Patents or Patent Applications to be Treated as Related". Jan. 31, 2022. 2 pages.
In re James T. Doubet, et al., U.S. Appl. No. 16/563,896, filed Sep. 8, 2019, Office Action, dated Jan. 10, 2020, 11 pages.
In re James T. Doubet, U.S. Appl. No. 16/393,696, filed Apr. 24, 2019, Office Action, dated Oct. 31, 2020, 16 pages.
In re James T. Doubet, U.S. Appl. No. 16/393,696, filed Apr. 24, 2019, Office Action, dated Jun. 27, 2019, 17 pages.
"List of Patents or Patent Applications to be Treated as Related". Aug. 10, 2021. 2 pages.
PCT Application PCT/US2019/036774, International Search Report dated Sep. 16, 2019 (2 pages).
PCT Application PCT/US2019/036774, Written Opinion of the International Searching Authority dated Sep. 16, 2019 (5 pages).
In re James T. Doubet, et al., U.S. Appl. No. 16/698,471, filed Nov. 27, 2019, Office Action, dated Nov. 10, 2020, 14 pages.
In re James T. Doubet, et al., U.S. Appl. No. 16/166,111, filed: Oct. 21, 2018, Office Action, dated Sep. 4, 2020, 20 pages.
In re James T. Doubet, et al., U.S. Appl. No. 16/203,858, filed Nov. 29, 2018, Office Action, dated Sep. 22, 2020, 25 pages.
In re James T. Doubet, et al., U.S. Appl. No. 16/563,896, filed Sep. 8, 2019, Office Action, dated Aug. 27, 2020, 21 pages.

* cited by examiner

FIG. 4
(Prior Art)
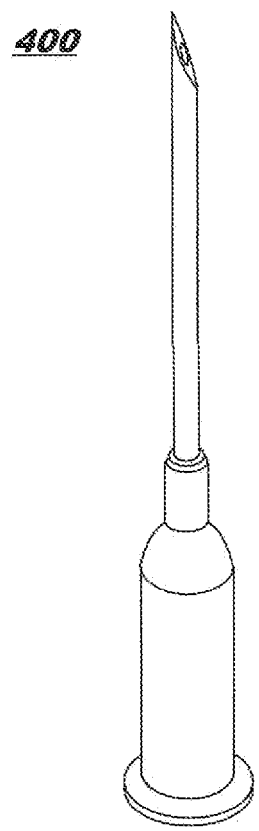
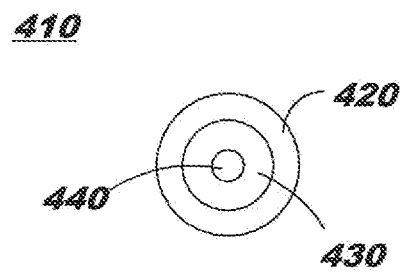
FIG. 4A
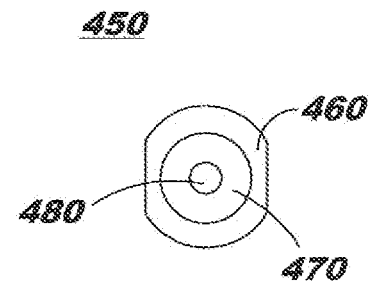
FIG. 4B

SECTION B-B

SECTION B-B

SECTION B-B

SECTION A-A

SECTION A-A

SECTION A-A

Exploded View

SECTION A-A

Exploded View

FIG. 22

|  | withdraw | expel |
|---|---|---|
| Test #1 | | |
| 18 gauge needle | 3 minutes 50.30 seconds | 35 seconds |
| 16 gauge needle | 35 seconds | 11 seconds |
| syringe adapter | 8 seconds | ---- |
| | | |
| Test #2 | | |
| syringe adapter | 5.54 seconds** | |
| | | |
| Test #3 | | |
| 16 gauge needle | 3 minutes 42.27 seconds | |
| syringe adapter | 1 minute 1 second | |

**Note: averaged over 5.76, 5.11, 4.64, 5.41, 5.97, 5.45 seconds after discarding 4.64 as an outlier

SYRINGE ADAPTER FOR MEDICATION

BACKGROUND

The present invention relates to improved apparatus for use with medication, and method(s) of using same, particularly for higher-viscosity medication.

Medication is needed for various purposes, including illness treatment and illness prevention.

BRIEF SUMMARY

The present invention is directed to improved apparatus for use with medication, and method(s) of using same, and is particularly useful for medication having a relatively high viscosity. In one aspect, a syringe adapter for withdrawing fluid medication from a container comprises a sidewall extending between a proximal end and a distal end, the sidewall having an interior surface defining a chamber, the proximal end configured to be connected to a syringe while withdrawing at least a portion of the fluid medication from the container through the chamber and into a barrel of the syringe and the distal end configured for inserting into the container for the withdrawal, wherein an opening at the distal end is relatively large in diameter to facilitate withdrawing fluid medication having a relatively high viscosity and the syringe adapter is configured to be removed from the syringe and replaced with a needle prior to subsequently injecting (for example, into an animal) the fluid medication (or at least some portion thereof) withdrawn into the barrel. The relatively large opening is directed toward improved syringeability of the fluid medication. The viscosity of the fluid medication is preferably greater than or equal to 50 centipoise units when a temperature of the fluid medication is at least 5 degrees Celsius.

The syringe is preferably configured as a pistol-grip syringe or a tab-handled syringe, and may therefore provide improved leverage for the subsequent injection. In an embodiment, the diameter of the opening at the distal end of the syringe adapter is preferably about 0.05 inches to about 0.1585 inches, and more preferably, this inner diameter is about 0.078 inches to about 0.14 inches, and even more preferably, is about 0.09 inches to about 0.11 inches, and generally, is approximately 0.10 inches. In an embodiment, the sidewall is approximately 0.05 inches in thickness at the distal end. Optionally, the syringe adapter further comprises a flanged area that extends laterally from the proximal end. Optionally, the syringe adapter may further comprise a radial extension member that extends perpendicularly and radially outward from an exterior surface of the syringe adapter. In an embodiment, an outer shape of the syringe adapter is generally conical in a first portion and generally cylindrical in a second portion. In an embodiment, an inner shape of the syringe adapter, for at least a portion of the proximal end, is generally conical. In an embodiment, the inner shape of the syringe adapter tapers from the proximal end toward the distal end, for at least a portion of the proximal end, at approximately 6 percent. The syringe adapter preferably connects to the syringe using a Luer-type connection, the Luer-type connection selected from the group consisting of a Luer-type lock and a Luer-type slip.

In another aspect, a method of administering fluid medication (for example, to an animal) comprises: affixing a syringe adapter to a syringe, the syringe adapter comprising a sidewall extending between a proximal end and a distal end, the sidewall having an interior surface defining a chamber, the proximal end configured to be connected to a distal end of the syringe; inserting the distal end of the syringe adapter into a container of fluid medication having a relatively high viscosity; withdrawing, from the container, at least a portion of the fluid medication through the chamber and into a barrel of the syringe, wherein an opening at the distal end of the syringe adapter is relatively large in diameter to facilitate withdrawing the relatively-high-viscosity medication; removing the syringe adapter from the syringe subsequent to the withdrawing; affixing a needle to the distal end of the syringe, subsequent to the removing; and injecting (for example, into an animal) the fluid medication (or at least some portion thereof) previously withdrawn into the barrel. The distal end opening is preferably about 0.05 inches to about 0.1585 inches, and more preferably, is about 0.078 inches to about 0.14 inches, and even more preferably, is about 0.09 inches to about 0.11 inches, and generally, is approximately 0.10 inches.

In yet another aspect, the syringe adapter is configured for receiving a needle at its distal end, such that the needle is affixed to the distal end of the syringe adapter subsequent to withdrawing fluid medication into the barrel of the syringe, and the syringe adapter is configured to remain in place while injecting the fluid medication (or at least some portion thereof) into a recipient with the needle. In this aspect, administering the fluid medication may be repeated (for example, for another recipient) by removing the needle, using the in-place syringe adapter for withdrawing more fluid medication (from the same or a different container), re-affixing the needle to the syringe adapter, and then injecting this medication (or some portion thereof). In this aspect, the distal end of the syringe adapter preferably provides for a Luer-type connection with the needle, and the proximal end of the syringe adapter is preferably configured with a Luer-type locking member for connecting to the syringe. The syringe adapter may further comprise an extension member that extends perpendicularly outward from an exterior surface of the syringe adapter.

In still another aspect, a syringe adapter for withdrawing viscous fluid medication from a container comprises a sidewall extending between a proximal end and a distal end opposite the proximal end, the sidewall having an interior surface defining a chamber, a first opening at the distal end being defined by a first end of the sidewall and a second opening at the proximal end being defined by a second end of the sidewall. In this aspect, the proximal end is configured to be connected to a distal end of a syringe, the distal end of the syringe having a third opening; the distal end of the sidewall of the syringe adapter is configured to be inserted into a container of viscous fluid medication; the first opening provides for fluid communication of the viscous fluid medication from the container into the chamber; the second opening provides for fluid communication of the viscous fluid medication between the chamber and, through the third opening, the barrel of the syringe; and the first opening has an inner diameter sized to facilitate withdrawing at least a portion of the viscous fluid medication through the first opening and into the chamber and then into the barrel. The inner diameter of the first opening is preferably about 0.05 inches to about 0.1585 inches, and more preferably, is about 0.078 inches to about 0.14 inches, and even more preferably, is about 0.09 inches to about 0.11 inches, and generally, is approximately 0.10 inches. Preferably, at least a portion of the viscous fluid medication is caused to be withdrawn from the container, through the first opening and into the chamber, and then through the second and third openings into the barrel, upon activation of a drawing mechanism of the syringe while the proximal end of the syringe adapter is connected to the syringe and while the distal end of the syringe adapter is inserted into the container.

In a further aspect, a method of withdrawing viscous fluid medication from a container comprises: affixing a syringe adapter to a syringe, the syringe adapter comprising a sidewall extending between a proximal end and a distal end opposite the proximal end, the sidewall having an interior surface defining a chamber, a first opening at the distal end being defined by a first end of the sidewall and a second opening at the proximal end being defined by a second end of the sidewall, the proximal end configured to be connected to a distal end of the syringe; inserting the distal end of the sidewall of the syringe adapter into a container of viscous fluid medication; and withdrawing, from the container, at least a portion of the viscous fluid medication through the first opening and into the chamber, and from the chamber through the second opening and then through a third opening in the distal end of the syringe and into a barrel of the syringe, wherein the first opening has an inner diameter sized to facilitate the withdrawing. The inner diameter of the first opening is preferably about 0.05 inches to about 0.1585 inches, and more preferably, is about 0.078 inches to about 0.14 inches, and even more preferably, is about 0.09 inches to about 0.11 inches, and generally, is approximately 0.10 inches. In this aspect, the syringe adapter is preferably configured to be removed from the syringe subsequent to the withdrawing and replaced by affixing a needle to the distal end of the syringe to thereby enable injecting, into a recipient with the needle, at least a portion of the viscous fluid medication withdrawn into the barrel.

In another aspect, the needle is removably affixed to a needle holder that, in turn, is removably affixed to the in-place syringe adapter for the injection. In an embodiment, the syringe adapter is configured with a support hub member for removably receiving the needle holder, the support hub member radially/laterally surrounding at least a portion of a length of a sidewall of the syringe adapter, the sidewall extending between a proximal end and a distal end opposite the proximal end, the sidewall having an interior surface defining a chamber, a first opening at the distal end being defined by a first terminal end of the sidewall and a second opening at the proximal end being defined by a second terminal end of the sidewall, wherein: a proximal end of the support hub member is configured for slipping over an exterior of a syringe tip located at a distal end of a syringe, the syringe tip having a third opening in a protrusion extending distally therefrom; the proximal end of the sidewall is configured to be connected to an internal threaded portion of the syringe tip, and to receive the protrusion within the chamber, while the proximal end of the support hub member is slipped over the exterior; the distal end of the sidewall is configured for inserting into a container of viscous fluid medication; the first opening provides for fluid communication of the viscous fluid medication from the container into the chamber; the second opening provides for fluid communication of the viscous fluid medication between the chamber and, through the third opening, a barrel of the syringe; the first opening has an inner diameter sized to facilitate withdrawing at least a portion of the viscous fluid medication through the first opening and into the chamber and then into the barrel; and a distal end of the support hub member, located opposite the proximal end of the support hub member, is configured for removably receiving a proximal end of a needle holder, the needle holder further comprising a distal end opposite the proximal end of the needle holder, the distal end of the needle holder adapted for removably affixing thereto a needle. The inner diameter of the opening at the distal end of the syringe adapter is at least about 0.05 inches, and is preferably about 0.05 inches to about 0.1585 inches, and more preferably, this inner diameter is about 0.078 inches to about 0.14 inches, and even more preferably, is about 0.09 inches to about 0.11 inches, and generally, is approximately 0.10 inches. In another embodiment, a syringe adapter for withdrawing viscous fluid medication comprises a support hub member radially/laterally surrounding an inner chamber, the syringe adapter further comprising an extension from a proximal end of the support hub member and a sidewall extending from a distal end of the support hub member, the distal end of the support hub member being opposite the proximal end of the support hub member, the inner chamber extending through the sidewall and the extension, a terminal end of the sidewall defining a first opening into the inner chamber and a terminal end of the extension defining a second opening into the inner chamber, wherein: a proximal end of the syringe adapter is affixed to a distal end of a syringe by inserting, into a cavity at the distal end of the syringe, the extension from the proximal end of the support hub member, wherein the cavity defines a third opening into the syringe; the terminal end of the sidewall is configured for inserting into a container of viscous fluid medication; the first opening provides for fluid communication of the viscous fluid medication from the container into the inner chamber; the second opening provides for fluid communication of the viscous fluid medication between the inner chamber and, through the third opening, a barrel of the syringe; the first opening has an inner diameter sized to facilitate withdrawing at least a portion of the viscous fluid medication through the first opening and into the inner chamber and then into the barrel; the distal end of the support hub member is configured for removably receiving a proximal end of a needle holder, the needle holder further comprising a distal end opposite the proximal end of the needle holder, the distal end of the needle holder adapted for removably affixing thereto a needle. The inner diameter of the first opening is at least about 0.05 inches, and is preferably about 0.05 inches to about 0.1585 inches, and more preferably, is about 0.078 inches to about 0.14 inches, and even more preferably, is about 0.09 inches to about 0.11 inches, and generally, is approximately 0.10 inches. In this aspect, the needle preferably remains affixed to the needle holder following an injection, whereby the needle may be removed from the syringe adapter (for example, in preparation for using the syringe adapter for withdrawing additional fluid medication from a container) by removing, as a single unit, the needle holder and the needle affixed thereto, and the needle holder preferably affixes to the distal end of the support hub member of the syringe adapter using a Luer-type locking connection.

In an aspect, a method of administering fluid medication comprises: inserting a distal end of a syringe adapter into a container of viscous fluid medication, the syringe adapter being affixed to a syringe, the syringe adapter comprising a support hub member radially/laterally surrounding at least a portion of a length of a sidewall, the sidewall extending between a proximal end and the distal end (the distal end being opposite the proximal end) and having an interior surface defining a chamber, a first opening at the distal end being defined by a first terminal end of the sidewall and a second opening at the proximal end being defined by a second terminal end of the sidewall, the syringe adapter configured to be affixed to the syringe by slipping a proximal end of the support hub member over an exterior of a syringe tip located at a distal end of the syringe, the syringe tip having a third opening in a protrusion extending distally therefrom, and connecting the proximal end of the sidewall to an internal threaded portion of the syringe tip; withdrawing, from the container, at least a portion of the viscous fluid medication through the first opening and into the chamber and then through the second and third openings into a barrel of the syringe; affixing a proximal end of a needle holder to a distal end of the support hub member, subsequent to the withdrawing from the container, the needle holder adapted for removably affixing a needle to a distal end thereof; and injecting, into a recipient with the needle affixed to the needle holder, at least a portion of the viscous fluid medication previously withdrawn into the barrel. An inner diameter of the first opening is at least about 0.05 inches, and is preferably about 0.05 inches to about 0.1585 inches, and more preferably, is about 0.078 inches to about 0.14 inches, and even more preferably, is about 0.09 inches to about 0.11 inches, and generally, is approximately 0.10 inches.

Various embodiments of these and other aspects of the present invention may be provided in view of the present disclosure. It should be noted that the foregoing is a summary and thus contains, by necessity, simplifications, generalizations, and omissions of detail; consequently, those of ordinary skill in the art will appreciate that the summary is illustrative only and is not intended to be in any way limiting. Other aspects, inventive features, and advantages of the present invention, as defined by the appended claims, will become apparent in the non-limiting detailed description set forth below.

BRIEF DESCRIPTION OF THE SEVERAL VIEWS OF THE DRAWINGS

The present invention will be described with reference to the following drawings, in which like reference numbers denote the same element throughout.

FIG. 4 depicts an example of a prior art needle;

FIGS. 4A and 4B illustrate bottom views showing how a proximal end of a needle may be configured for securable attachment to a syringe;

FIGS. 16 and 17 illustrate a needle holder adapted for a locking connection with the needle;

FIG. 22 presents tables containing measurements from tests conducted to compare use of a sample version of the disclosed syringe adapter to use of conventional needles.

DETAILED DESCRIPTION

Figure 1:
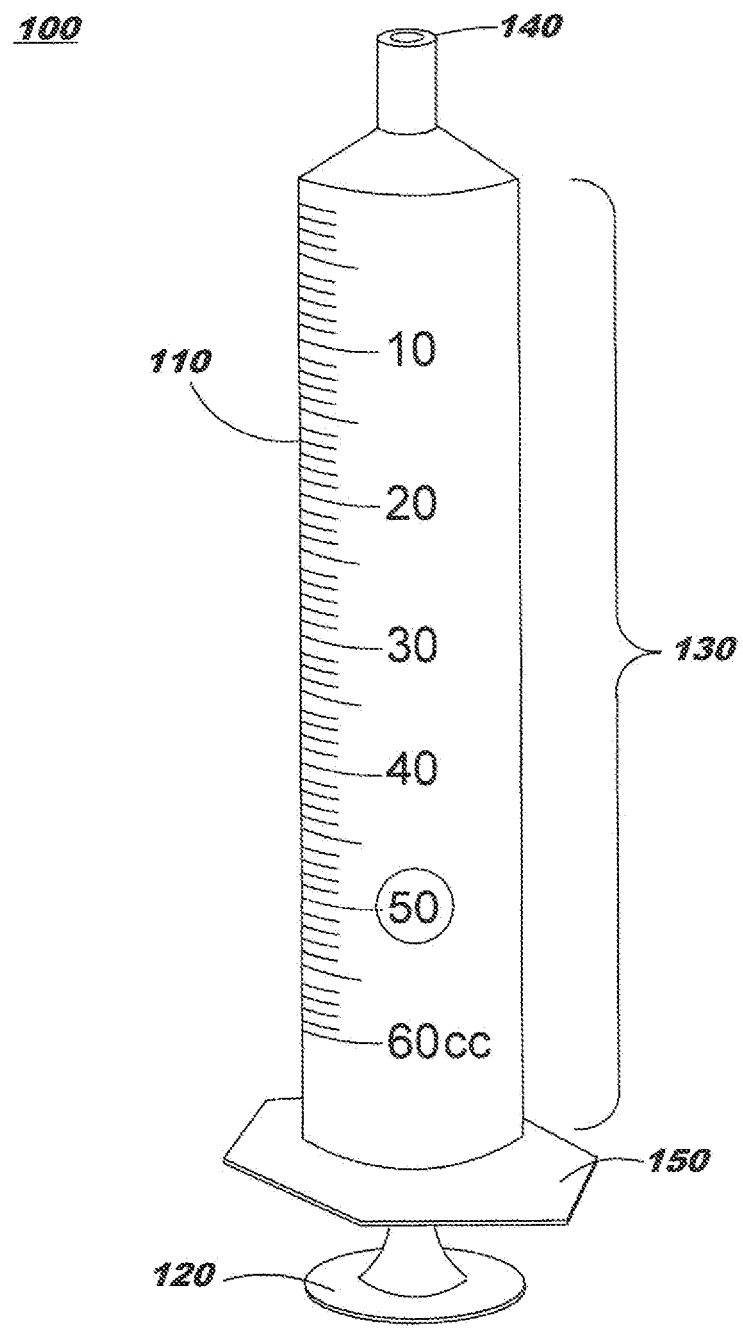
FIGS. 1-3 depict examples of prior art syringes.

As noted earlier, medication is needed for various purposes, including illness treatment and illness prevention. Discussions are presented herein with reference to medication used for animals, primarily in terms of livestock animals; this is by way of illustration and not of limitation, however, and it should be noted that the disclosed syringe adapter may be beneficial with medication used for all types of animal life, including humans.

Treatment of animals using medication may be desired whether the animal is a family pet, part of a livestock operation, is the subject of research, and so forth. Examples of medicating animals for illness treatment will be obvious, and may span a wide variety of illnesses. One example of medicating an animal for illness prevention is a proactive vaccination; another example is to proactively administer an antibiotic. In a commercial livestock operation, animals may be proactively medicated before they are introduced into another group of livestock, for example to guard against introducing an illness that they may carry or simply to ensure that all animals in the group have received an identical medication regimen. Medication might also be administered in anticipation of, or in response to, a change in weather conditions or a change in geographical location for an animal (such as moving from one climate to another). Hereinafter, animal medications are discussed without differentiation of the purpose for such medication.

Medication may be found in various forms, including solid and fluid. Solid substances may be ingestible, for example, while fluids may be injectable or may be administered orally or nasally. Embodiments of the present invention are directed toward improved apparatus for use with medication in fluid form, and the scope of the present invention also includes method(s) for using such apparatus.

Medications provided in fluid form may vary widely in their viscosity, depending upon their chemical formulation. Viscosity is sometimes defined as the resistance of a substance to flow. The viscosity of water is relatively low, for example, while the viscosity of honey is relatively high. The viscosity of some substances can be changed by applying heat; for example, melting butter increases its ability to flow. Some fluid medications may have a viscosity that is relatively low and is similar to that of water, for example, and thus will flow quite easily. Other fluid medications are known that have a viscosity that is markedly different from water.

Fluid medications intended for use with animals are commonly marketed in multi-dose packaging, such as bottles that hold enough fluid for administering several doses. A bottle of medication might hold 500 milliliters, for example (equivalently, 500 cubic centimeters), which is roughly equivalent to 16.9 ounces. The bottle might be made of glass or plastic, and a container having a configuration other than a bottle might be used. Hereinafter, the term "bottle" is used for ease of reference, and by way of illustration and not of limitation, as a container type in which medication may be contained.

One reason for marketing animal medication in multi-dose bottles is economic. The cost of the medication may be reduced, for example, by selling a larger quantity container and thereby reducing the relative cost of the packaging. Another reason for marketing animal medication in multi-dose bottles is that the dosage of many (if not all) medications is prescribed with regard to the animal's body weight. Accordingly, the correct amount of medication to use on a particular animal can be calculated and then withdrawn from the multi-dose bottle, after which it may be injected into the animal, and the remaining medication is then available for subsequent use.

A multi-dose bottle of fluid medication is typically marketed with a rubber membrane covering at least a portion of an opening at the top of the bottle. Conventionally, the fluid medication is withdrawn from such bottle by placing a needle onto the tip of a syringe, inserting a tip of the needle into the rubber membrane, and withdrawing a plunger of the syringe until an appropriate amount of fluid is pulled into the syringe body (referred to herein as the syringe "barrel"); this same needle is then used for injecting the medication from the syringe into the animal. FIG. 1 shows an example of a prior art syringe 100, and illustrates how the hollow barrel 130 of syringe 100 is commonly marked with fill lines 110 that are provided for measuring the amount of fluid contained therein. A needle is placed over (or inside) the tip 140, and fluid enters through an opening or eye of the needle and into the syringe barrel 130. The syringe includes a retractable plunger, a terminal end of which is shown at 120. (As will be obvious, as fluid medication is withdrawn from the bottle into the barrel 130, the plunger 120 movably extends outward from the proximal end of the syringe 100, although this is not illustrated in FIG. 1.) Commonly, a syringe as illustrated in FIG. 1 is constructed of plastic, making it relatively cheap to purchase.

A tab-shaped member 150 is also provided on syringe 100. When administering the medication from the barrel 130, a person's index finger is placed on the tab-shaped member 150 at one side of barrel 130 and the person's middle finger is placed on the tab-shaped member 150 at the opposing side of barrel 130, and the person's thumb is then used to depress the terminal end of plunger 120 into the barrel in order to expel the medication from the barrel.

Figure 2:
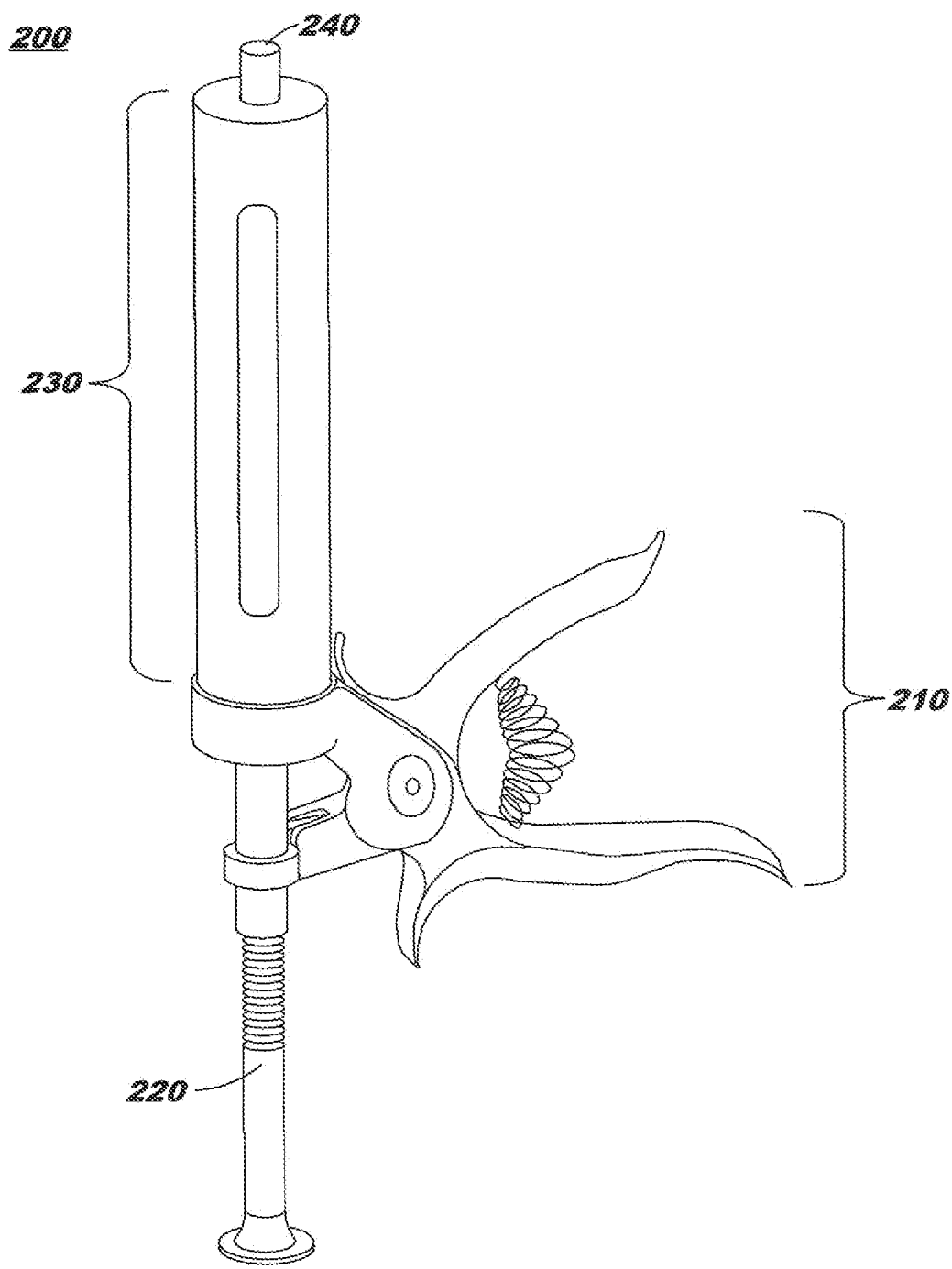

As an alternative to the syringe 100 of FIG. 1, an example of a so-called "pistol-grip" syringe is illustrated in FIG. 2. Fluid medication is drawn into a syringe of this type by pulling plunger 220 outwardly from the barrel 230. A tab-shaped member is not provided on a syringe of this type, as compressing or squeezing the handles 210 serves to expel medication from the barrel of a syringe having a pistol-grip configuration.

Figure 3:
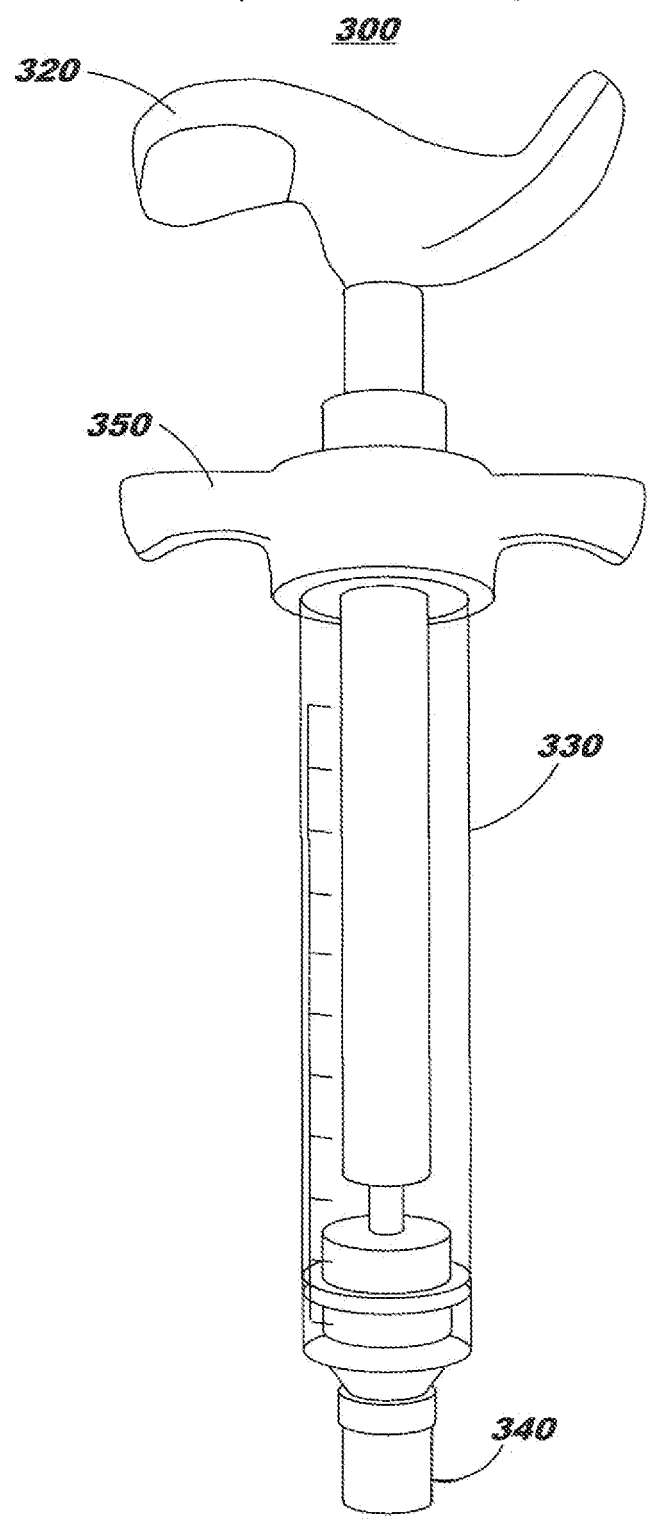

FIG. 3 illustrates yet another prior art syringe 300, and is referred to herein as a "tab-handled" syringe. In this configuration, the syringe has a tabbed member 350 near the proximal end of barrel 330, and includes a handle-style tabbed member 320 affixed to the terminal end of the plunger. The tabbed member 350 is used in a similar manner to tab-shaped member 150 of FIG. 1, whereby a person places fingers on the tabbed member 350 on opposing sides of barrel 330; the person then presses down on tabbed member 320 using the person's palm to depress the terminal end of the plunger into the barrel in order to expel the medication from the barrel. As will be readily understood, fluid medication is drawn into a syringe of this type by pulling handle 320 to thereby draw the attached plunger outwardly from the barrel 330. As compared to tab-shaped member 150 and plunger end 120 of FIG. 1, the tabbed members 320, 350 of FIG. 3 typically provide improved comfort for the person using the tab-handled syringe.

The tips 240, 340 may be generally on the order of ⅜ to 7/16 inch in diameter and generally of similar height (and similarly, tip 140), and are generally constructed of metal. An interior area of this tip is intended for securably attaching a needle and is generally threaded for at least a portion thereof. A height of this threaded area is believed to be generally on the order of ⅛ inch to ¼ inch (and it is believed that a height of 5.4 millimeters, or approximately 0.2125 inches, is used for syringe tip threads that conform to ISO 80369-7:2016, which is further discussed below). While not illustrated in detail on tips 240, 340 of FIGS. 2 and 3, the syringe tip also typically includes a protrusion (illustrated herein in FIGS. 14D, 15D, 16D, and 17D; see reference number 341) that is centered within the exterior wall of the tip and that provides the opening through which a substance enters into the syringe barrel. See, for example, the syringe tip opening location denoted by reference number 349 in FIG. 16D. (Notably, tips 140, 240, 340 are not designed for inserting through the rubber membrane of a medicine bottle.)

Syringes 200, 300 are often constructed, at least in part, of metal. Glass or plastic might be used for the syringe barrel. A metal commonly used for syringes, by way of example, is stainless steel; another example is aluminum.

FIG. 4 illustrates an example of a prior art needle 400, which may be affixed to the distal end of syringes 100, 200, or 300. Needles are typically sold in standardized sizes, and thus the distal syringe ends 140, 240, 340 typically conform to the standard size of the proximal end of a needle. FIGS. 4A and 4B illustrate bottom views showing examples of how a proximal end of needle 400 may be configured for securable attachment to the distal end of a syringe that has an internal threaded portion. In an approach 410 as shown in FIG. 4A, a flanged area 420 extends radially outward from the proximal end of the needle (as is generally illustrated in FIG. 4). Reference number 440 depicts the opening in the tip of the needle, and reference number 430 generally depicts the sidewall of needle 400. In another approach 450 as shown in FIG. 4B, a flanged area 460 extends perpendicularly outward from the proximal end of the needle, but in this configuration, is fashioned as having tabs as side edges that are not generally round. (Note that it is believed that the flanged area 460 of a needle extends perpendicularly, although more generally, this will be understood as a "lateral" extension. Accordingly, references herein to a "perpendicular" extension for connecting to a syringe should be interpreted more generally as a "lateral" extension for making such connection.) Reference number 480 depicts the opening in the tip of the needle, and reference number 470 generally depicts the sidewall of needle 400. In either case, a flanged area 420, 460 on the proximal end of a needle is designed to securably attach to a corresponding receiving area on the distal end of a syringe. In yet another approach (not illustrated), the securable attachment of a needle to a syringe tip relies on friction instead of an exterior flanged area, whereby the proximal end of needle 400 is placed over an exterior of the distal end (e.g., tip 140 of FIG. 1) of a syringe. These approaches are commonly referred to as a Luer-style lock approach and a Luer-style slip approach, respectively, as is discussed in further detail below. (As is readily understood, a Luer-style lock relies upon a threaded attachment of what are commonly denoted as "male" and "female" parts, which may be achieved by placing tabs as lateral extensions on one part, these tabs designed to rotatably descend within corresponding threads of the other part.) Note that if flanged area 420 is configured to extend perpendicularly outward as illustrated in FIG. 4A, it is preferably intended for use in a Luer-type slip connection rather than a Luer-type lock connection, due to the so-called "double start" or double helix configuration that is described for the internal threads of a Luer-type lock hub according to International Standards 594-1:1986 and ISO 594-2:1998(E) and their replacement ISO 80369-7:2016, which are discussed in further detail below. As an alternative, tabs may be added to the outer edge of flanged area 420, where these tabs are configured for engaging the internal threads of the Luer-type lock hub (and specifications pertaining to such tabs are provided in ISO 80369-7:2016).

For withdrawing fluid medication from a bottle into the barrel of syringe 100, 200, or 300 using known techniques, the sharp tip at the distal end of the needle 400 is inserted through the rubber membrane of the bottle. For subsequently administering the fluid medication from the barrel of the syringe, the sharp tip of that same needle is inserted into an animal's body, and the person holds tab-shaped member 150 while simultaneously depressing plunger 120 of syringe 100, squeezes the handles 210 of pistol-grip syringe 200, or holds tabbed member 350 while simultaneously depressing handle-style tabbed member 320 of tab-handled syringe 300.

This known approach of withdrawing fluid medication from a bottle using a needle and then administering the medication using the same needle works well for fluids having a low viscosity. (Consider, by way of reference, the relative ease of drawing a low-viscosity fluid such as water through the tip/opening of a needle 400 affixed to a syringe.) However, animal medications are marketed that have a relatively high viscosity (that is, they are relatively thick in consistency), and this higher viscosity makes the medications very difficult to withdraw from a bottle using a needle, and also typically more difficult to expel from the syringe. Stated another way, such higher-viscosity medications are not readily "syringeable".

When a medication is not readily syringeable, it may take a considerable amount of time for the person tasked with withdrawing the medication from the bottle to withdraw even a small amount of medication. When a large amount of such medication must be administered, and/or when the higher-viscosity medication must be administered to multiple animals, the person may experience frustration or even fatigue due to this long withdrawal time. As a result, use of the higher-viscosity medication by animal care-givers may be diminished, which may lead to the medication failing to reach its potential market share. Thinning the medication is undesirable as an answer to improving the syringeability problem, as the effectiveness of the medication could be altered.

In addition to the above-described issues with withdrawing higher-viscosity medication into a syringe, the higher viscosity of the medication makes the injection process more time-consuming and physically more difficult for the person tasked with medicating the animal. In particular, the general configuration of a plastic syringe as illustrated in FIG. 1 does not enable a person using the syringe to have sufficient leverage when attempting to inject the medication into an animal. Tab-shaped member 150 is known to collapse or break in some instances, due to the physical force that must be exerted while depressing plunger 120. The plunger shaft is also known to break in some instances, for example due to misalignment as it moves within the barrel or due to age-related brittleness. The needle may also be forced off the syringe when attached thereto by a friction-based Luer-type slip connection, which may in turn lead to leakage and/or waste of the medication through the now-opened end of the syringe. Additionally, the syringe tips of plastic syringes are known to break off while medicating an animal (for example, due to the animal moving or thrashing about), which can lead to waste of medication in the syringe. These problems are more likely to occur with the increased physical force required for injecting higher-viscosity medications.

In sharp contrast to use of a plastic syringe, the syringes 200, 300 of FIGS. 2-3 are better adapted for withstanding the physical force required for expelling a higher-viscosity medication from the syringe barrel and for allowing the person using the syringe to have better leverage during the injection process. Because the leverage is improved, the time required to complete the injection may be shortened as compared to use of a plastic syringe configured as shown at 100 of FIG. 1, which benefits the person and the animal.

In view of the above-described issues, preferred embodiments of the present invention are directed toward improved syringeability of medications having a relatively high viscosity. The disclosed syringe adapter may function suitably with lower-viscosity medications as well, and is therefore not deemed to be limited to use with particular medications.

A preferred embodiment of the present invention provides a new tip that operates as a syringe adapter for withdrawing medication from a bottle. This tip is preferably affixed to a pistol-grip syringe of the type illustrated in FIG. 2 or a tab-handled syringe of the type illustrated in FIG. 3. The pistol-grip or tab-handled syringe may be formed from plastic, metal, or other substance(s), as noted earlier. Accordingly, use of an embodiment of the present invention addresses the issue of drawing a higher-viscosity fluid from a bottle as well as the issue of providing sufficient leverage for subsequent injection. That is, the larger opening of the disclosed syringe adapter (as compared to a conventional needle) addresses syringeability issues by improving draw time of higher-viscosity medications and, when this adapter is affixed to a pistol-grip or tab-handled syringe, the medication withdrawn into the pistol-grip or tab-handled syringe can be more easily administered from the syringe barrel (noting that, in some embodiments, the syringe adapter will be replaced with a needle prior to injecting the medication).

While discussions herein refer to preferably using the disclosed syringe adapter with a pistol-grip or tab-handled syringe, it should be noted that the disclosed syringe adapter may also be used advantageously with a syringe of the type shown in FIG. 1 (and such usage is within the scope of the present invention).

Figure 5:
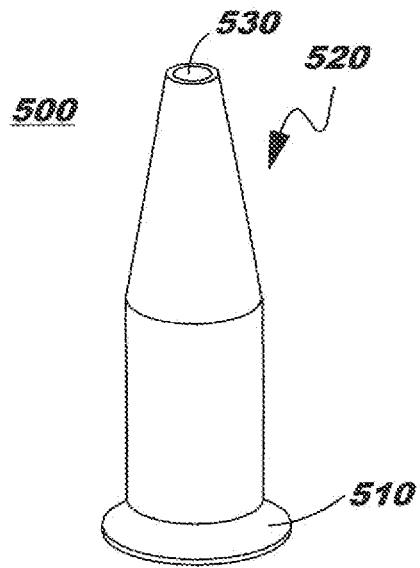
FIGS. 5-6 illustrate first and second preferred embodiments of the syringe adapter disclosed herein.

FIG. 5 illustrates one embodiment of the syringe adapter disclosed herein. The syringe adapter has a sidewall extending between a proximal end (i.e., the end on which reference number 510 is located) and a distal end (denoted generally at 520), and the interior surface of the sidewall defines a chamber through which fluid medication flows. Reference number 530 denotes the location of the opening in the distal end of syringe adapter 500. The length and shape of the syringe adapter, as well as the thickness of portions of the sidewall and the width of its interior chamber, may vary from illustrations depicted herein without deviating from the scope of the present invention. In the embodiment illustrated in FIG. 5, the shape of the syringe adapter 500 is generally conical in an upper portion and generally cylindrical in a lower portion. While not illustrated in FIG. 5, an interior of at least a portion of the lower portion is preferably tapered, with a 6 percent taper extending from the proximal end toward the distal end. This tapered shape conforms the interior surface to the above-noted International Standards ISO 594-1:1986 and ISO 594-2:1998(E) and their replacement ISO 80369-7:2016, which are directed toward conical fittings for health-care applications. Preferably, the overall length of the syringe adapter is not shorter than ⅜ to ½ inch, by way of illustration but not of limitation, as this length will enable the syringe adapter to sufficiently extend into a bottle of medication to be withdrawn. An upper range of the overall length, conversely, may be on the order of 1 to 2 inches, by way of illustration but not of limitation.

A preferred diameter of the hole in the distal end of the tip of the syringe adapter is on the order of 0.10 inches, although embodiments are not limited to this diameter (and as discussed in further detail hereinafter, the diameter used in embodiments of the present invention is preferably about 0.05 inches to about 0.1585 inches, and more preferably, is about 0.078 inches to about 0.14 inches, and even more preferably, is about 0.09 inches to about 0.11 inches, and generally, is approximately 0.10 inches). Thickness of the sidewall of the syringe adapter is preferably on the order of 0.050 inches, although embodiments are not limited to this thickness. Using a sidewall thickness of 0.050 inches and an opening of 0.10 inches results in a syringe adapter having an overall diameter of 0.20 inches at the end to be inserted into the bottle of medication, in this example configuration. The above-cited International Standards indicate that sidewall thickness for a Luer tip (whether Luer-type lock or Luer-type slip) that conforms to the International Standards may range between 0.021 inches as a minimum and 0.039 inches as a maximum. Accordingly, in another example configuration, an embodiment of the syringe adapter may use a sidewall thickness of about 0.03 inches and an opening sized at 0.09 inches, in which case the outer diameter at the end to be inserted into the bottle is 0.15 inches. Advantageously, it is noted that the opening formed by the sidewall at the distal end of the syringe adapter is depicted herein for several embodiments as generally blunt, as contrasted with a sharp metal point found on the tip of a needle, thereby improving safety for someone who may, for example, carry a syringe adapter on his or her person. (FIGS. 17-19, discussed below, depict embodiments where the opening is not generally blunt.)

Preferably, the proximal end of the disclosed syringe adapter attaches to a syringe using a Luer-type lock or a Luer-type slip (although it will be understood that this is by way of illustration and not of limitation). Luer-type locks and Luer-type slips are known approaches for making leak-free connections on fluid fittings, and are described in the above-cited International Standards. A Luer-type lock provides a threaded attachment, whereby two pieces of a configuration are held together by rotating a flanged area (such as flanged area 460 of FIG. 4B) of one piece within threads of the other piece, whereas a Luer-type slip is non-threaded and provides attachment using friction. In one approach for securably attaching syringe adapter 500 using a Luer-type lock, the syringe adapter 500 as illustrated in FIG. 5 has an external flanged area 510 on the proximal end (shown without tabs extending from the outer edge, for drafting convenience), and a two-part connection is made by inserting this flanged end into corresponding internal threads on a distal end of a syringe (as discussed above with reference to the syringe tips illustrated at 240, 340). As noted earlier, a conventional height for this internal threaded portion of a pistol-grip or tab-handled syringe tip is believed to be approximately ⅛ inch to ¼ inch in length and a standardized height thereof is believed to be 5.4 millimeters, and accordingly, a flanged area 510 on the proximal end of syringe adapter 500 is preferably on the order of at least 1/16 to ⅛ inch in height. The shape of flanged area 510 may correspond generally to flanged area 420 or 460 (for example, by extending radially or perpendicularly from the proximal end of the syringe adapter, although a strictly circular shape is not required), although another shape providing for a securable attachment may be used without deviating from the scope of the present invention. (In view of this ability to use shapes other than strictly circular for securable attachment, it will be readily understood that references herein to "radial" or "radially" may be more generally understood as "lateral" or "laterally".) Notably, with regard to the securable attachments noted herein that are described as preferably using a Luer-lock connection, it will be readily understood that the shape and size of the attachment area—such as the area denoted in FIG. 5 by reference number 510—preferably conforms to the well-known shape and size required for such connection.

In another approach, the proximal end of the syringe adapter 500 may omit the flanged area shown at 510 and is attached and held to the distal end of the syringe by friction in a Luer-type slip approach.

Figure 6:
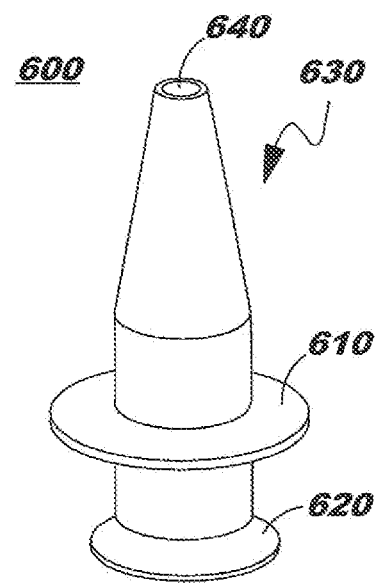

FIG. 6 illustrates another embodiment of the syringe adapter disclosed herein. In this embodiment, syringe adapter 600 includes a radial extension feature 610, which is preferably configured as extending perpendicularly and radially outward from the body of the syringe adapter and is shown in FIG. 6 as being located relatively near to the proximal end of syringe adapter 600 (where the proximal end of syringe adapter 600 is the end on which reference number 620 is located, and the distal end is denoted generally by reference number 630; reference number 640 denotes the location of the opening in this distal end). Alternatively, radial extension feature 610 may be placed at another location on the syringe adapter, for example being located closer to the conical portion thereof. In addition to enabling a person to more easily grasp the syringe adapter 600, the radial extension feature 610 also serves to prevent inserting the syringe into the medication bottle far enough that the attachment point (e.g., Luer-type slip or lock) between the syringe and the syringe adapter would come into contact with the medication. Stated another way, an extension feature (or equivalently, "extension member") on an embodiment of the disclosed syringe adapter is preferably sized so as to halt insertion of the syringe adapter into the container beyond a location of the extension feature. Accordingly, in a preferred embodiment, a diameter of radial extension feature 610 is sufficiently large as to meet or exceed the diameter of a conventional rubber membrane on a medicine bottle, although it will be understood that embodiments are not limited to this diameter. The diameter of radial extension feature 610 may be, by way of example, on the order of twice the diameter of the cylindrical portion of syringe adapter 600. (Syringe adapter 600 may omit the flanged area 620 when relying on a Luer-type slip attachment, and is depicted without tabs extending from the outer edge for drafting convenience, as was discussed above with reference to flanged area 510.)

An extension feature might alternatively be used that is not round, although this has not been illustrated in FIG. 6.

(For example, a hexagonal shape might be used for an extension feature, and in view of this ability to use an extension feature that is not round, it will be readily understood that references herein to a "radial" extension feature are by way of illustration but not of limitation and are not to be construed as requiring the extension feature to have a round outer edge. More generally, the extension feature may be termed a "lateral" extension feature or simply an "extension feature".) As noted above, a preferred diameter for an extension feature as disclosed herein (as illustrated by the example at reference number 610) is selected to provide compatibility with a size of the rubber membrane on a bottle from which fluid will be withdrawn. It will be readily understood that a common diameter of the rubber membrane fitted in the top of bottles holding 250 milliliters ("ml") of fluid and also bottles holding 500 ml is 0.75 inches. (Most common multi-dose fluid medication bottles are sold in bottles having volumes of 100 ml, 250 ml, and 500 ml, while some less-common smaller-dose bottles hold 20 ml of fluid.) It is readily understood that a common outer diameter of the top of such bottles is about 1.3 inches. Accordingly, a preferred diameter for the extension feature when used with such bottles is in the range of about 0.50 inches to about 1.3 inches, and more preferably, the diameter is about 0.70 inches to about 0.80 inches, and most preferably, is about 0.75 inches as noted herein. The range in size for the extension feature has been selected, through experimentation and testing, by noting that an extension feature diameter appreciably exceeding the outer width of the medicine bottle may be cumbersome for the person holding the bottle and the syringe with affixed syringe adapter, and that an extension feature diameter about the diameter of the rubber membrane—or ranging between about the diameter of the rubber membrane and about the outer diameter of the top of the bottle—provides an advantageous size that allows the person to grip the outer edges of the extension feature while also gripping the bottle, and at the same time, also ensuring that the extension feature is unlikely to push through the rubber membrane. If used with a bottle having other dimensions than those noted above, it will be understood that the diameter of the extension feature may be adapted to provide compatibility therewith. In such adaptation, it is preferred that the diameter of the extension feature is preferably within about the diameter of the rubber membrane and about the outer diameter of the top of the bottle, and more generally, ranges between about two-thirds the diameter of the rubber membrane and about the diameter of the top.

A preferred material for the disclosed syringe adapter is plastic, which will allow it to be economically produced as a disposable item, although another material may be used without deviating from the scope of the present invention. As one alternative to use of plastic, the syringe adapter or portion(s) thereof may be constructed from stainless steel, aluminum, or another metal (or combinations thereof), noting that metal generally provides increased strength and durability as compared to plastic. It will be readily understood that constructing the syringe adapter from a material such as plastic advantageously allows it to be recyclable, in addition to being easily disposable (as contrasted to disposal of a sharp needle, for which care must be taken upon disposal to ensure that, inter alia, persons or animals are protected from injury therefrom). Notably, the disclosed syringe adapter does not need to come into physical contact with a particular animal (i.e., because the physical contact occurs at the needle used to inject the medication), and thus re-use of the syringe adapter for medicating multiple animals need not introduce cross-contamination concerns.

Figure 7:
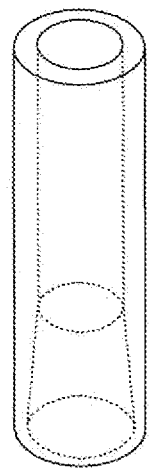
FIGS. 7-8 illustrate alternative embodiments of the syringe adapter disclosed herein.
Figure 8:

While FIGS. 5 and 6 illustrate a syringe adapter shape that is generally conical in an upper portion and generally cylindrical in a lower portion, this is by way of illustration and not of limitation. As one alternative embodiment, an outer shape of the syringe adapter may be generally cylindrical while still preferably having a tapered interior shape for at least a portion of the proximal end as in the embodiments illustrated in previously-discussed FIGS. 5 and 6, noting that such interior taper enables the syringe adapter to comply with the above-cited International Standards. This alternative embodiment is illustrated in FIG. 7, where dotted lines are used to illustrate a general shape of the interior. FIG. 8 provides another alternative embodiment, where an outer shape of the syringe adapter may be generally conical in an upper portion and generally cylindrical in a lower portion, and in this alternative, the relative length of the upper and lower portions varies from the embodiments illustrated in FIGS. 5 and 6 (and again, at least a portion of such configuration preferably has a tapered interior shape at the proximal end, as shown by the dotted lines, to thereby conform to the above-cited International Standards). Notably, as compared to the cylindrical exterior shape as illustrated in FIG. 7, the exterior taper of the upper portion as illustrated in FIGS. 5-6 and 8 may tend to provide a better seal, and thus be less likely to leak, during such time as the syringe adapter is inserted through the rubber membrane of a bottle. While not illustrated in FIG. 7 or 8, a radial extension member (such as that shown at reference number 610 of FIG. 6) may be added to these configurations if desired.

Figure 9:
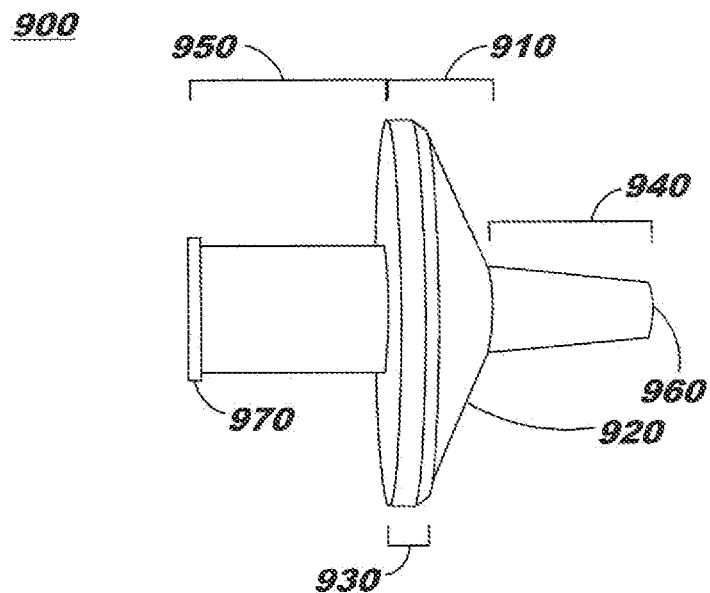
FIG. 9 illustrates a still further embodiment of the syringe adapter disclosed herein.

FIG. 9 illustrates yet another embodiment of the disclosed syringe adapter. In this embodiment, syringe adapter 900 includes a radial extension feature 910, similar to the previously-discussed radial extension feature 610 of FIG. 6. FIG. 9 depicts radial extension feature 910 as being located approximately midway along the length of the syringe adapter, by way of illustration but not of limitation. Whereas the radial extension feature illustrated at 610 of FIG. 6 is illustrated as having a disk-like shape with generally flat upper and lower surfaces, FIG. 9 illustrates an alternative shape where an upper surface of the radial extension feature 910 has a somewhat domed or tapered shape. This tapered or domed portion is shown at reference number 920 and sits atop a disk-like portion 930. Optionally, the lower surface of the radial extension feature may taper in addition to, or instead of, the upper surface thereof, although this has not been illustrated. (Note that the particular shape and dimensions of portions 920, 930 may vary, and thus FIG. 9 provides one example by way of illustration but not of limitation.)

FIG. 9 also illustrates the upper portion 940, at the distal end, of the syringe adapter 900 as having a generally conical shape which is somewhat less tapered than the upper portion as illustrated for the syringe adapters 500, 600 of FIGS. 5 and 6, and having a generally cylindrical shape for the lower portion 950, located at the proximal end of syringe adapter 900. Reference number 960 denotes the location of the opening in the distal end of syringe adapter 900. (As noted below with regard to FIG. 10, the proximal end of the syringe adapter preferably makes a Luer-type lock connection with the tip of a syringe, and it will therefore be readily understood that the shape illustrated at 970 is merely an example and is not to be construed as limiting.)

By way of illustration but not of limitation, a length of the conical portion 940 may be 0.32 inches; a length of the cylindrical portion 950 may be 0.48 inches; a height or thickness of portion 930 may be 0.07 inches; a diameter of radial extension feature 910 may be 0.75 inches; a diameter of the distal and proximal ends of conical portion 940 may be 0.156 inches and 0.174 inches, respectively; and a diameter of cylindrical portion 950 may be 0.24 inches. (When using the above-noted example sidewall thickness of 0.05 inches, and if the thickness is uniform throughout, it will be noted that these illustrative measurements indicate an example where the inner diameter of the cylindrical portion 950 is 0.14 inches and the inner diameter of the distal and proximal ends of conical portion 940 are 0.056 inches and 0.074 inches, respectively.)

Figure 10:
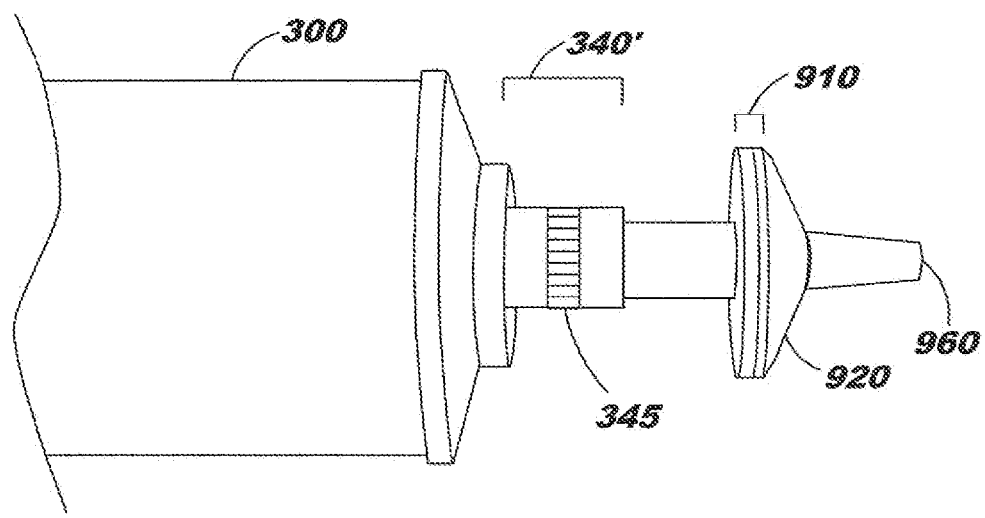
FIG. 10 illustrates a syringe adapter placed upon a syringe.

FIG. 10 illustrates placement of a syringe adapter on a syringe. By way of illustration but not of limitation, the syringe in FIG. 10 corresponds to the tab-handled syringe 300 of FIG. 3 and the syringe adapter corresponds to the embodiment shown at 900 of FIG. 9. Syringe tip 340' provides a point of attachment for the syringe adapter 900, and syringe tip 340' is shown as being generally cylindrical; as contrasted with syringe tip 340 as earlier illustrated, syringe tip 340' is shown with a ribbed exterior mid-section 345 that may provide for a person to securely grip the syringe tip 340' while the syringe adapter 900 is being inserted therein (or removed therefrom). The connection between syringe tip 340' and syringe adapter 900 is preferably a Luer-type lock, but a Luer-type slip may be used alternatively without deviating from the scope of the present invention. (It will be understood that in FIG. 10, a portion of the proximal end of syringe adapter 900 is located inside the distal end of tip 340', following the connection.)

Figure 11:
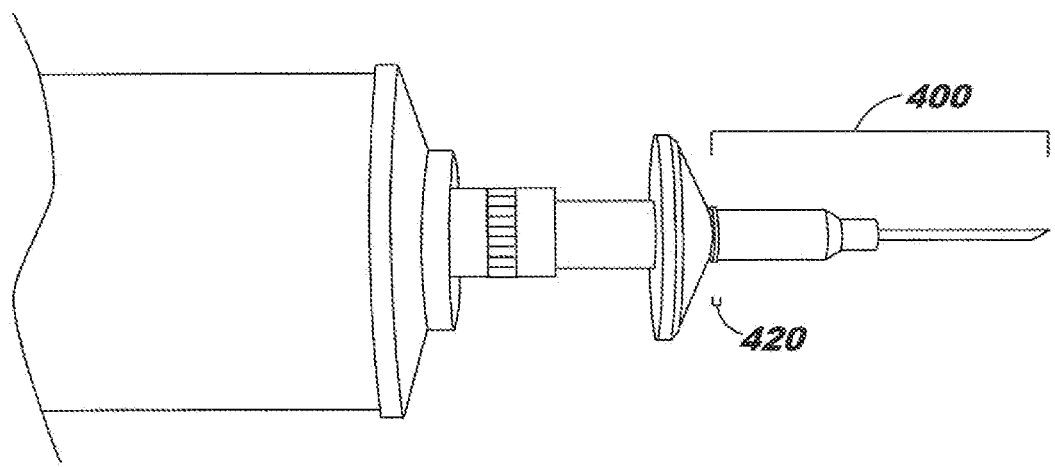
FIG. 11 illustrates a needle placed upon a syringe adapter.

FIG. 11 illustrates one example of placement of a needle on a syringe adapter, for an embodiment in which the syringe adapter remains in place while medication is administered through an attached needle. By way of illustration but not of limitation, the syringe adapter in FIG. 11 corresponds to the embodiment shown at 900 of FIG. 9, the attachment between the syringe and syringe adapter 900 corresponds to the attachment illustrated in FIG. 10, and the needle corresponds to the needle 400 of FIG. 4. In FIG. 11, needle 400 is shown as having its proximal end placed over the distal end of the syringe adapter. In this example, needle 400 includes a small flanged area 420 that enables it to securably attach to the interior of a Luer-type lock, although the illustrated attachment in FIG. 11 is a Luer-type slip connection. Accordingly, the needle 400 may be attached to, and removed from, the syringe adapter with relative ease (e.g., by pushing the proximal end of the needle onto the distal end of the syringe adapter and pulling it therefrom, respectively). Note that while flanged area 420 is shown as directly abutting the portion of the syringe adapter shown as having a domed shape, this is by way of illustration: alternatively, there may be a gap beneath flanged area 420.

Figure 12:
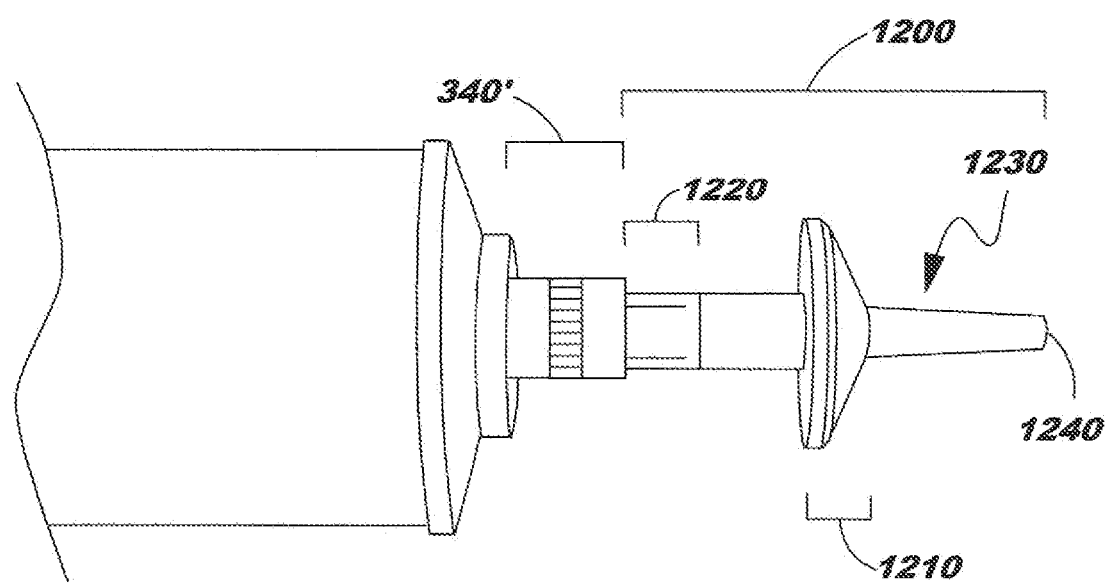
FIGS. 12 and 13 illustrate yet other embodiments of the syringe adapter disclosed herein, and also illustrate placement thereof upon a syringe.

FIG. 12 illustrates still another embodiment of the disclosed syringe adapter, and its placement on a syringe. In this embodiment, syringe adapter 1200 includes a radial extension feature 1210 with a tapered or domed upper surface, similar to the previously-discussed radial extension feature 910 of FIG. 9. As contrasted to syringe adapter 900, the conical portion of the syringe adapter 1200 is somewhat longer (and it should be noted that embodiments of the present invention are not limited to a specific dimension, as has been discussed).

FIG. 12 also illustrates a Luer-type connecting member 1220 affixed to the proximal end of syringe adapter 1200 (where 2 horizontally-oriented "ribs" are illustrated on an upper portion of the surface of member 1220, by way of illustration but not of limitation, and may serve as a grasping member that assists a person using the syringe adapter in firmly grasping). This connecting member 1220 is shown in FIG. 12 as connecting syringe adapter 1200 to a syringe, which may be syringe 300 of FIG. 3 (by way of illustration but not of limitation). The point of connection on syringe 300 is shown in FIG. 12 as comprising a syringe tip 340', similar to that which was discussed above with reference to FIG. 10 by way of illustration, into which the proximal end of connecting member 1220 of syringe adapter 1200 is removably inserted. In one approach, connecting member 1220 is made from metal while remaining portions of syringe adapter 1200 are made from plastic, and a bond is made between the metal and plastic during manufacturing. Preferably, connecting member 1220 attaches to syringe tip 340' with a Luer-type lock connection (rather than a Luer-type slip connection). While not shown in FIG. 12, connecting member 1220 preferably includes a flanged area at its proximal end (such as flanged area 460 of FIG. 4B), and the Luer-type lock connection is made by inserting this flanged area of connecting member 1220 into syringe tip 340' and then twisting the syringe adapter 1200 until the flanged area locks into place in the internal threaded portion of the syringe tip 340'. This type of connection is deemed beneficial for providing a more secure attachment between the syringe and the syringe adapter. Reference number 1220 generally denotes the proximal end of syringe adapter 1200, although as stated above, a portion of the proximal end is located within syringe tip 340' and is therefore not visible. Reference number 1230 generally denotes the distal end of syringe adapter 1200, while reference number 1240 denotes the location of the opening therein.

Figure 13:
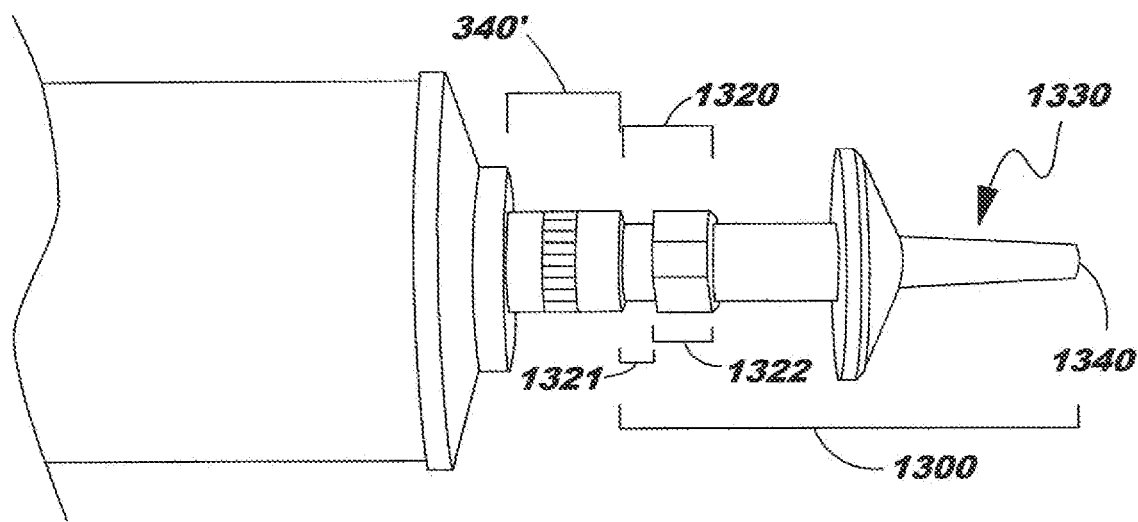
Figure 14A:
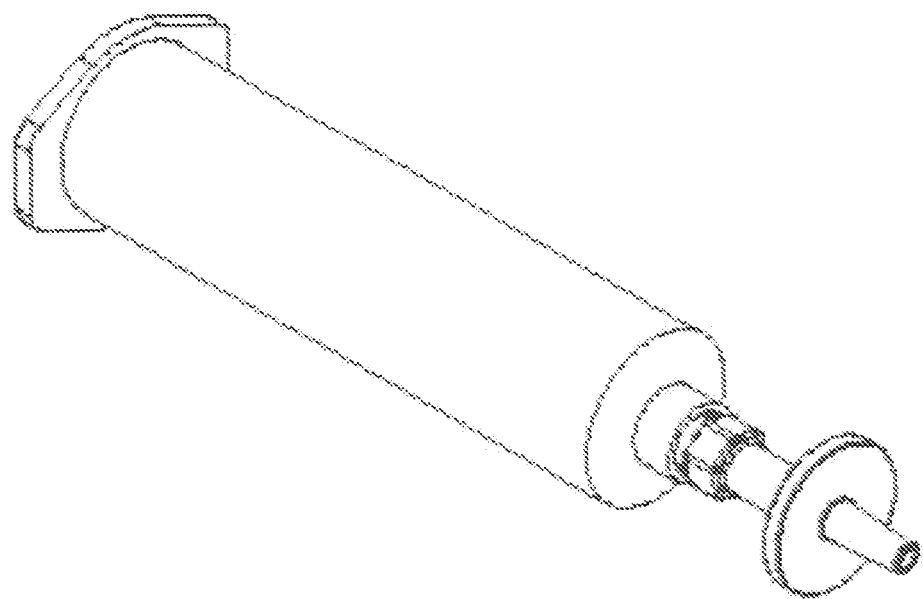
FIG. 14 (comprising FIGS. 14A through 14D) illustrates a further embodiment of the disclosed syringe adapter, showing exterior views as well as cross-sectional views of placement thereof upon a syringe and as exploded.
Figure 14B:
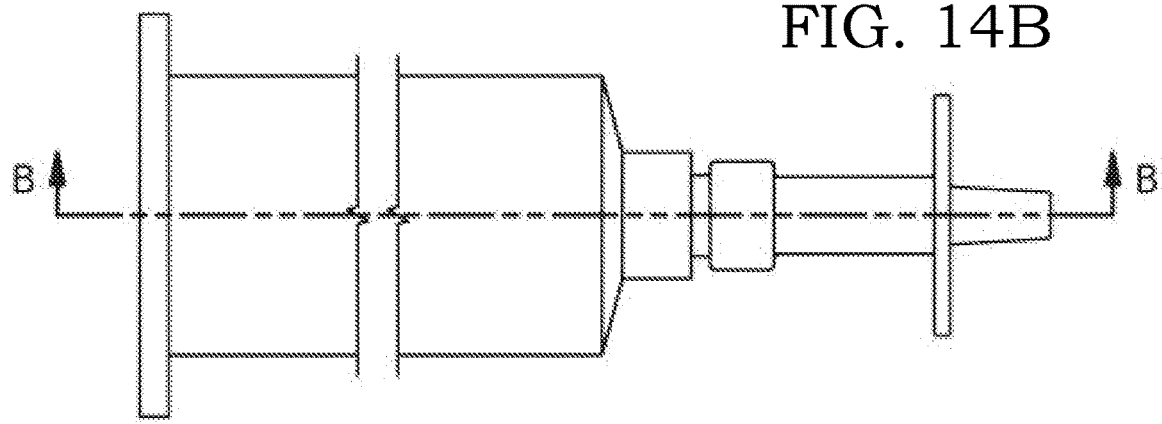
Figure 14C:
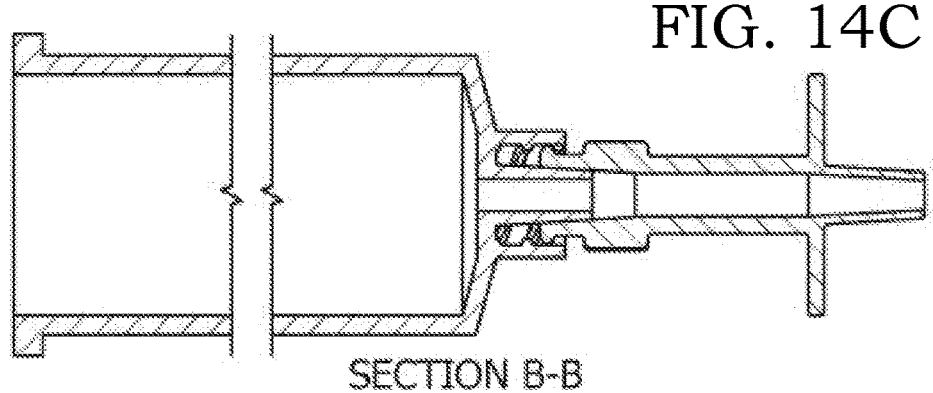
Figure 14D:
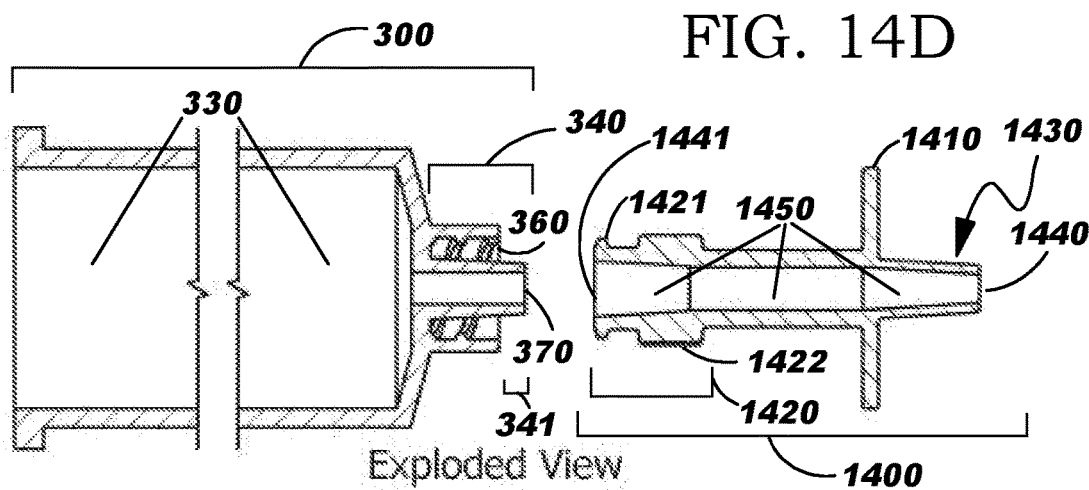

FIG. 13 illustrates yet another embodiment of the disclosed syringe adapter and its placement on a syringe. In this embodiment, syringe adapter 1300 differs from syringe adapter 1200 of FIG. 12 in that a Luer-type connecting member 1320 affixed to the proximal end of syringe adapter 1300 uses a different configuration. As shown in FIG. 13, an upper portion 1322 of connecting member 1320 has a multi-sided exterior shape, shown by way of illustration as being hexagonal in at least a portion thereof, which may serve as a grasping member that assists a person using the syringe adapter in firmly grasping. More particularly, in the example shown in FIG. 13, connecting member 1320 has a hexagonal upper portion 1322 and a cylindrical lower portion 1321. In one approach, connecting member 1320 is made from metal while remaining portions of syringe adapter 1300 are made from plastic, and a bond is made between the metal and plastic during manufacturing. Preferably, connecting member 1320 attaches to syringe tip 340' with a Luer-type lock connection (rather than a Luer-type slip connection). While not shown in FIG. 13, connecting member 1320 preferably includes a flanged area at its proximal end (such as flanged area 460 of FIG. 4B), and the Luer-type lock connection is made by inserting this flanged area of connecting member 1320 into syringe tip 340' and then twisting the syringe adapter 1300 until the flanged area locks into place in the internal threaded portion of the syringe tip 340'. As noted above, the Luer-type lock connection is deemed beneficial for providing a more secure attachment between the syringe and the syringe adapter. Reference number 1320 generally denotes the proximal end of syringe adapter 1300, although as stated above, a portion of the proximal end is located within syringe tip 340' and is therefore not visible. Reference number 1330 generally denotes the distal end of syringe adapter 1300, while reference number 1340 denotes the location of the opening therein.

FIG. 14 (comprising FIGS. 14A through 14D) illustrates a further embodiment of the disclosed syringe adapter, showing exterior views as well as cross-sectional views of placement thereof upon a syringe and as exploded. By way of illustration but not of limitation, the syringe in FIG. 14 corresponds to the tab-handled syringe 300 of FIG. 3 with its syringe tip 340. Syringe adapter 1400, in this embodiment, includes a radial extension member 1410 and the proximal end as denoted by reference number 1420 includes a Luer-type connecting member, where proximal end 1420 in turn includes a flanged area 1421 at its proximal end (such as flanged area 460 of FIG. 4B) for removably attaching syringe adapter 1400 to the distal end of syringe 300 and an upper portion 1422. The Luer-type lock connection is made by inserting flanged area 1421 of proximal end 1420 into syringe tip 340 and then twisting the syringe adapter 1400 until the flanged area 1421 locks into place in the internal threaded portion 360 of the syringe tip 340 (as illustrated in the non-exploded cross-sectional view of FIG. 14C) to thereby provide a secure attachment between the syringe and the syringe adapter. It is noted that the above-cited International Standard ISO 80369-7 states acceptable measurements for inner and outer diameters of male and female portions of components intended for a Luer-type connection. For example, inside diameter for a male connector is stated as a range between 2.100 millimeters and 2.900 millimeters (i.e., 0.082677 inches and 0.114173 inches), and outside diameter for a male connector is stated as ranging between 3.970 millimeters and 4.072 millimeters (i.e., 0.156299 inches and 0.160315 inches), with a nominal outside diameter of 4.021 millimeters (i.e., 0.158307 inches); dimensions for corresponding female connectors are stated as roughly 0.20 millimeters smaller. In an embodiment, inner and outer diameters of flanged area 1421 are preferably designed for compatibility with such measurements to enable syringe adapter 1400 to make a secure attachment to the internal threaded portion of a syringe tip 340 that is manufactured in conformance with such measurements. As noted above with reference to the ribs at 1220 and upper portion 1322, upper portion 1422 may serve as a grasping member that assists a person using the syringe adapter with firmly grasping (for example, while inserting and twisting the flanged area 1421 into the syringe tip 340). Reference number 370 denotes the opening in syringe tip 340, which provides a fluid communication path with syringe barrel 330. Reference number 1430 generally denotes the distal end of syringe adapter 1400, while reference number 1440 denotes the location of the opening therein. (It will also be understood that reference number 1430 points to the sidewall of syringe adapter 1400.) Reference number 1441 denotes the location of the opening in proximal end 1420. Reference number 1450 denotes the location of the chamber defined by the interior surface of the sidewall in syringe adapter 1400, the chamber extending between the proximal end opening 1441 and the distal end opening 1440. (As can be seen with reference to FIGS. 14C and 14D, embodiments are not limited to using a uniform sidewall thickness throughout.)

FIG. 15 illustrates a still further embodiment of the disclosed syringe adapter, showing exterior views as well as cross-sectional views of placement thereof upon a syringe and as exploded. The embodiment illustrated in FIG. 15 includes a needle holder to which a needle may be removably affixed. In this embodiment, a needle 400' (illustrated as having an outer shape somewhat different from needle 400, by way of illustration but not of limitation) is removably affixed to a needle holder 1510 that, in turn, is removably affixed to a syringe adapter 1500 that is removably affixed to a syringe 300 for the injection of medication into a recipient. When the injection is completed, the needle 400' preferably remains affixed to the needle holder 1510, enabling needle 400' and needle holder 1510 to be removed from syringe adapter 1500 as a single unit (for example, in preparation for using syringe adapter 1500 for withdrawing additional fluid medication from a container). This enables the combination of needle holder and needle to be quickly and easily re-installed on the syringe adapter, after the syringe adapter is used for withdrawing a next dosage of medication, for administering that next dosage if the needle is deemed to be reusable for that next dosage. While discussions herein of embodiments using a needle holder as depicted in FIGS. 15-21 refer to the possibility of reusing a needle that has been attached to the needle holder, it is recognized that needle reuse is not advisable in some situations, such as when there is a risk of cross-contamination. In such situations, the used needle is preferably removed from the needle holder of FIGS. 15-21 and replaced with an unused needle. (It should be noted that the cross-sectional views in FIG. 15 illustrate a preferred interior and exterior shape of components 1500, 1510, but embodiments are not limited to the specific shapes and/or relative dimensions as shown except as otherwise noted herein. It should also be noted that the syringe adapters as described herein with reference to FIGS. 15-21 have separate utility without use of the corresponding needle holder; that is, the syringe adapters illustrated in FIGS. 15-21 provide benefits analogous to those discussed herein with regard to the embodiments illustrated in FIGS. 5-14.)

Preferably, syringe adapter 1500 is configured with a support hub member 1501 that radially surrounds at least a portion of the length of the syringe adapter sidewall 1502. Preferably, the connection of syringe adapter 1500 to syringe tip 340 is made as a Luer-type lock by inserting a flanged proximal end 1504 of syringe adapter sidewall 1502 into an internal threaded portion of syringe tip 340 (as illustrated at 360 of FIG. 14C) and then twisting the syringe adapter 1500 until the flanged area locks into place in the internal threaded portion 360 (see FIG. 14C) of the syringe tip 340. A proximal end of support hub member 1501 (i.e., the end where reference number 1501 is generally located) is preferably sized so as to slip over the exterior of syringe tip 340, while the proximal end of syringe adapter sidewall 1502 (i.e., the end where reference number 1504 is generally located) is sized so as to fit within the threaded interior of syringe tip 340 and to receive protrusion 341 of the syringe tip 340 within the chamber defined by the interior surface of sidewall 1502. This is illustrated in the non-exploded cross-sectional view of FIG. 15C. (Similarly, with reference to FIGS. 16 and 17, it can be seen that syringe adapter embodiments 1600, 1700 preferably connect to syringe tip 340 by inserting a flanged proximal end 1604, 1704 of sidewall 1602, 1702 into an internal threaded portion 360 of syringe tip 340, and that the proximal end of support hub member 1601, 1701 is preferably sized so as to slip over the exterior of syringe tip 340 while the flanged proximal end 1604, 1704 of syringe adapter sidewall 1602, 1702 is sized so as to fit within the threaded interior 360 of syringe tip 340 and to receive protrusion 341 within the chamber defined by the interior surface of sidewall 1602, 1702.) As discussed above with reference to FIG. 14, it is noted that the above-cited International Standard ISO 80369-7 states acceptable measurements for inner and outer diameters of male and female portions of components intended for a Luer-type lock connection. In an embodiment, inner and outer diameters of support hub member 1501 and flanged proximal end 1504 are preferably designed for compatibility with such measurements to enable syringe adapter 1500 to make a secure attachment to the internal threaded portion of a syringe tip 340 that is manufactured in conformance with such measurements, and similarly for support hub members 1601, 1701 and flanged proximal ends 1604, 1704 of syringe adapters 1600, 1700.

Figure 15A:
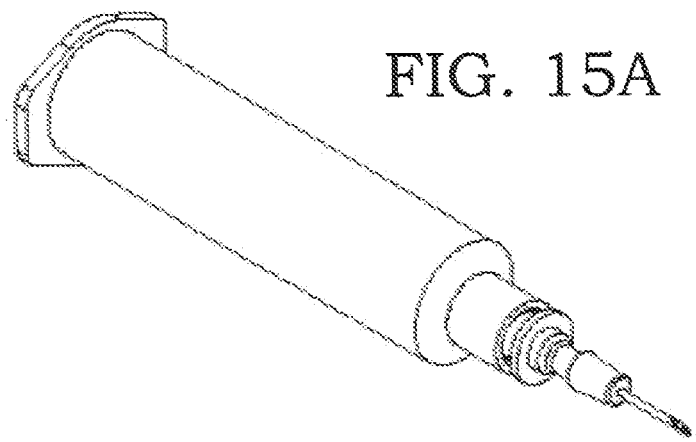
FIG. 15 (comprising FIGS. 15A through 15D) illustrates a still further embodiment of the disclosed syringe adapter that includes a needle holder to which a needle may be removably affixed, showing exterior views as well as cross-sectional views of placement thereof upon a syringe and as exploded.
Figure 15B:
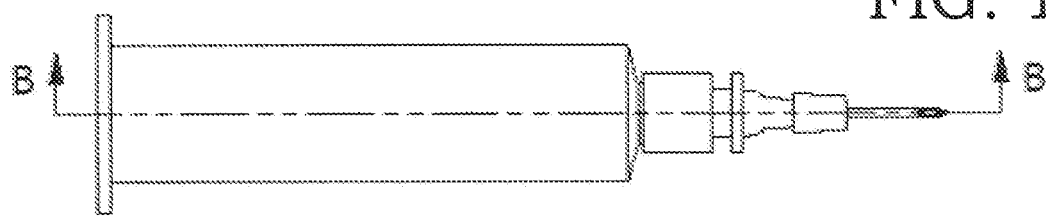

In an embodiment, the opening 1509 at the distal end of sidewall 1502 (noting that the distal end of sidewall 1502 is the end at which reference number 1502 is generally located) is approximately 0.10 inches in inside diameter (and as discussed in further detail hereinafter, the diameter is preferably about 0.05 inches to about 0.1585 inches, and more preferably, is about 0.078 inches to about 0.14 inches, and even more preferably, is about 0.09 inches to about 0.11 inches, and generally, is approximately 0.10 inches), and this distal end of sidewall 1502 extends beyond the distal end of support hub member 1501 (i.e., the end of support hub member where reference number 1503 is generally located) to allow the distal end of sidewall 1502 to penetrate the rubber membrane on the medication bottle. In an embodiment, an outer wall of support hub member 1501 is shaped as a cylinder (as illustrated in FIG. 15A). In another embodiment, by way of illustration but not of limitation, the outer wall may be configured to have a multi-sided exterior shape (such as, for example, a hexagonal shape, and in view of this ability to use shapes other than strictly cylindrical for the exterior shape, it will be readily understood that references herein to a support hub member that "radially surrounds" or is "radially surrounding" may be more generally understood as "laterally surrounds" or is "laterally surrounding").

A distal end of support hub member 1501 is preferably configured with an internal threaded portion to facilitate removably attaching needle holder 1510. The threads are illustrated in FIG. 15 generally by small extensions 1503 on the interior wall of support hub member 1501, and this internal threaded portion receives a flanged area 1511 (similar to the above-described flanged area 460 of FIG. 4B, which may alternatively be referred to as a tabbed area) that is located at the proximal end of needle holder 1510. In an embodiment, the threads illustrated by extensions 1503 correspond to a double-helix configuration as described in the above-cited International Standards. Needle holder 1510 thereby makes a Luer-type lock connection with syringe adapter 1500. In a configuration as illustrated in FIG. 15, support hub member 1501 also provides additional support for needle holder 1510. See the non-exploded cross-sectional view in FIG. 15C.

Needle holder 1510 preferably includes a radial extension feature 1512, which may be located (by way of example) near the proximal end of the needle holder (noting that the proximal end of needle holder 1510 is the end where reference number 1511 is generally located, and the distal end of the needle holder is opposite thereto). Radial extension feature 1512 may enable a person to more easily grasp the needle holder 1510. In a configuration as illustrated in FIG. 15, radial extension feature 1512 also serves to provide additional strength for the needle holder 1510, and thus may reduce the likelihood of a physical failure during use.

Figure 15C:
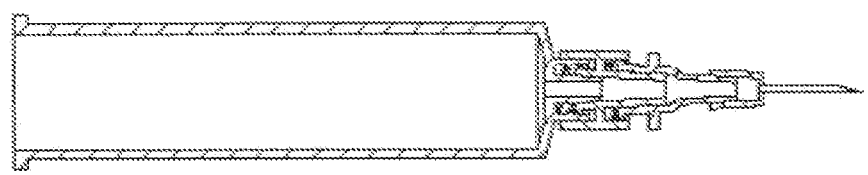
Figure 15D:
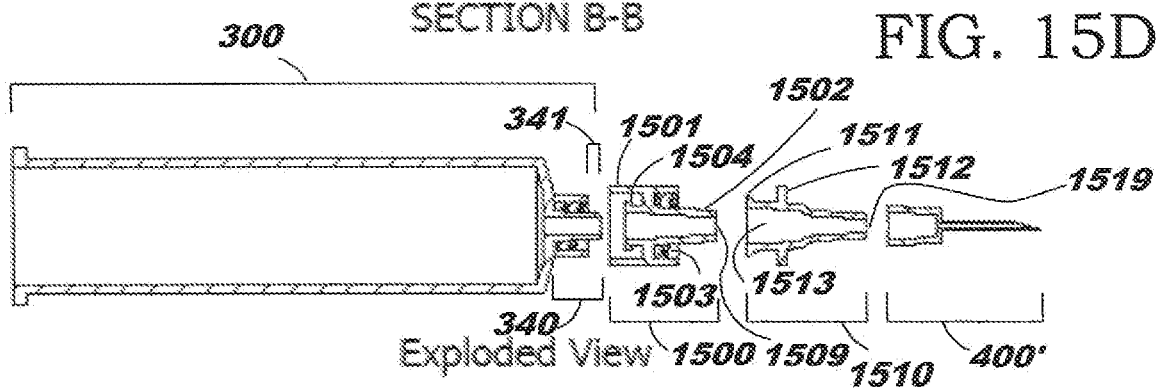

Needle holder 1510 is configured for removably attaching a needle 400', and is illustrated in FIG. 15 as using a Luer-type slip connection that makes the attachment by placing the proximal end of needle 400' over the distal end of needle holder 1510 (as illustrated by FIGS. 15C and 15D). Needle holder 1510 may alternatively be configured to support a Luer-type lock connection with needle 400' without deviating from the scope of the present invention, although this is not illustrated in FIG. 15. Such alternative configuration for a needle holder may be used with syringe adapter 1500, in place of needle holder 1510, within the scope of the present invention. (FIGS. 16-21, discussed below, illustrate embodiments that use Luer-type lock connections between a needle and needle holder.)

Preferably, syringe adapter 1500 and needle holder 1510 are constructed from a plastic or a composite. Syringe adapter 1500 and/or needle holder 1510 may alternatively be constructed from another material, such as stainless steel, aluminum, or another metal (or a combination thereof), without deviating from the scope of the present invention— although as discussed earlier, using a material such as plastic for the syringe adapter and needle holder advantageously allows these components to be recyclable.

Syringe adapter 1500 may optionally be configured as a permanent attachment to (or replacement for) syringe tip 340, rather than being removably affixed thereto. (See the discussion of FIGS. 18-21, below, which depict embodiments that replace a conventional syringe tip.) A distal end of the sidewall 1502 of syringe adapter 1500 may be relatively sharp, for ease of inserting this distal end into a bottle of medication (for example), as contrasted to the generally blunt opening that is illustrated for this embodiment in FIG. 15D. (See the discussion of FIGS. 17-19, below, which depict embodiments having a relatively sharp tip—i.e., a tip that is not generally blunt—on the distal end of a syringe adapter.)

In an embodiment, the opening 1519 at the distal end of needle holder 1510 is approximately 0.08 inches in inside diameter (see, for example, the above-noted reference to male connectors ranging between 2.100 and 2.900 millimeters), and the outside diameter of the distal end of needle holder 1510 preferably conforms to suggested dimensions for a Luer-type tip in the above-cited International Standards to thereby facilitate connection to standard needles. Accordingly, in an embodiment, while the inner diameter for opening 1519 is approximately 0.08 inches as noted above, outer diameter is preferably about 0.16 inches to accommodate a Luer-type slip connection to a needle 400' that is manufactured in conformance with such measurements. In an embodiment as illustrated in FIG. 15, an outer wall of needle holder 1510 has a conical shape at the distal end and a similar shape at the proximal end, where both the proximal end and the distal end are generally conical in shape. Preferably, a length of an inner chamber 1513 of needle holder 1510 extends from the attachment point in support hub member 1501 to cover the distal end of syringe adapter 1500 (as illustrated in the non-exploded cross-sectional view in FIG. 15C). Note that while the needle holder 1510 and needle 400' may be removed as a unit from the syringe adapter 1500, this is by way of example; alternatively the needle may be removed from the needle holder and the needle holder may then be removed from the syringe adapter, without deviating from the scope of the present invention.

FIG. 16 illustrates yet another embodiment of the disclosed syringe adapter, showing exterior views as well as cross-sectional views of placement thereof upon a syringe and as exploded. The embodiment illustrated in FIG. 16 includes a needle holder to which a needle may be removably affixed. In this embodiment, a needle 400 is removably affixed to a needle holder 1610 that, in turn, is removably affixed to a syringe adapter 1600 that is removably affixed to a syringe 300 for the injection of medication into a recipient. When the injection is completed, the needle 400 preferably remains affixed to the needle holder 1610, enabling needle 400 and needle holder 1610 to be removed from syringe adapter 1600 as a single unit (for example, in preparation for using syringe adapter 1600 for withdrawing additional fluid medication from a container). This enables the combination of needle holder and needle to be quickly and easily re-installed on the syringe adapter, after the syringe adapter is used for withdrawing a next dosage of medication, for administering that next dosage. (It should be noted that the cross-sectional views in FIG. 16 illustrate a preferred interior and exterior shape of components 1600, 1610, but embodiments are not limited to the specific shapes and/or relative dimensions as shown except as otherwise noted herein.)

Figure 16A:
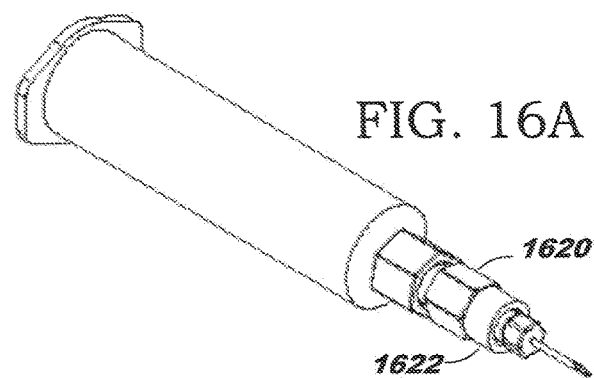
FIGS. 16 (comprising FIGS. 16A through 16D) and 17 (comprising FIGS. 17A through 17D) illustrate yet other embodiments of the disclosed syringe adapter that include a needle holder to which a needle may be removably affixed, showing exterior views as well as cross-sectional views of placement thereof upon a syringe and as exploded, where
Figure 16B:
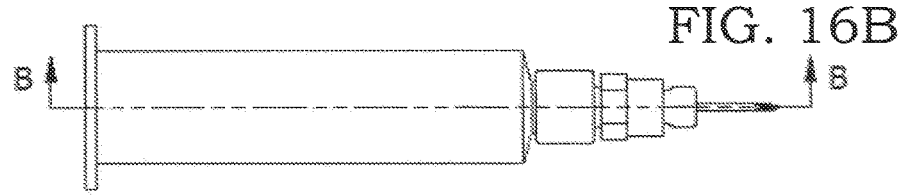
Figure 16C:
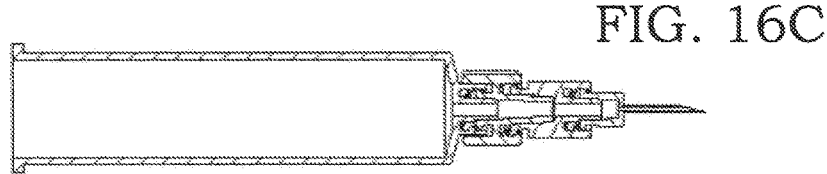
Figure 16D:
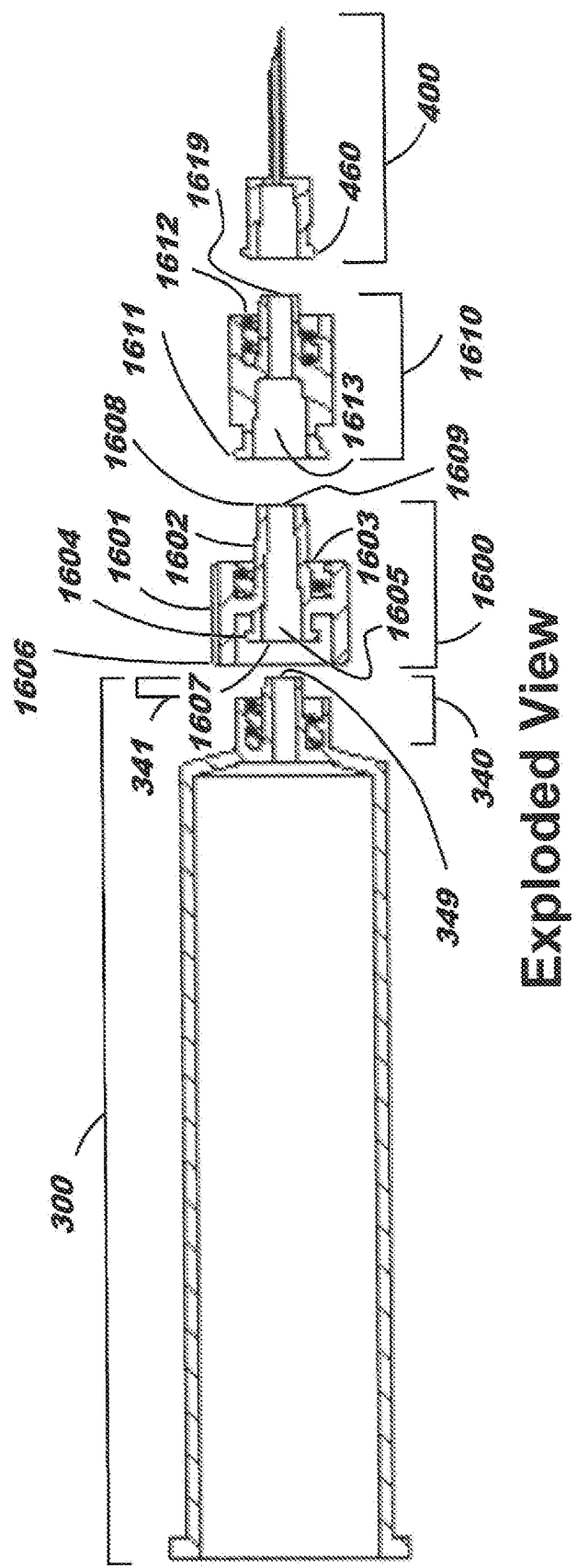

Preferably, syringe adapter 1600 is configured with a support hub member 1601 that radially surrounds at least a portion of the length of the syringe adapter sidewall 1602. In an embodiment as illustrated in FIG. 16, the exterior of the outer wall of support hub member 1601 has a hexagonal shape (as shown in FIG. 16A). This hexagonal shape may enable a person to have a better grasp when connecting or disconnecting the syringe adapter 1600 to syringe 300 and/or needle holder 1610. (Note that while FIG. 16A illustrates the exterior of support hub member 1601 as being hexagonal in shape, this is by way of illustration but not of limitation, and the exterior may be configured to have a different shape without deviating from the scope of the present invention.)

A Luer-type lock connection between syringe adapter 1600 and syringe tip 340 is preferably made in the manner discussed above with reference to FIG. 15, and accordingly, details of the connection are not repeated here in full. A result of the connection is illustrated in the non-exploded cross-sectional view in FIG. 16C.

In an embodiment, the opening 1609 at the terminal end 1608 of the distal end of sidewall 1602 (noting that the distal end of sidewall 1602 is the end at which reference number 1602 is generally located, and reference number 1604 denotes a flanged proximal end of sidewall 1602) is approximately 0.10 inches in inside diameter (and as discussed in further detail hereinafter, the diameter is preferably about 0.05 inches to about 0.1585 inches, and more preferably, is about 0.078 inches to about 0.14 inches, and even more preferably, is about 0.09 inches to about 0.11 inches, and generally, is approximately 0.10 inches), and this distal end of sidewall 1602 extends beyond the distal end of support hub member 1601 (i.e., the end where reference number 1603 is generally located, the proximal end of support hub member 1601 being opposite thereto) to allow the distal end of sidewall 1602 to penetrate the rubber membrane on the medication bottle. Reference number 1604 denotes a flanged proximal end of sidewall 1602, and reference number 1607 denotes the opening at the flanged proximal end 1604. (It can be seen that the flanged proximal end 1604 is a terminal proximal end of sidewall 1602.) Reference number 1605 denotes the chamber defined by the interior surface of sidewall 1602.

A distal end of support hub member 1601 (i.e., the end where reference number 1603 is generally located) is preferably configured with an internal threaded portion, similar to the threaded portion discussed above with reference to support hub member 1501 of FIG. 15, and a Luer-type lock connection between syringe adapter 1600 and needle holder 1610 is preferably made using the threads (illustrated in FIG. 16 generally by small extensions 1603) and the flanged area 1611 (which may alternatively be referred to as a tabbed area) at the proximal end of needle holder 1610 in the manner discussed above with reference to FIG. 15. See the non-exploded cross-sectional view in FIG. 16C. The proximal end of support hub member 1601 is denoted by reference number 1606.

Needle holder 1610 is configured for removably attaching a needle 400. Needle holder 1610 includes an internal threaded portion (see reference number 1612) on its distal end (i.e., the end where reference number 1612 is generally located), where these threads are configured to provide a Luer-type lock connection with the flange 460 at the proximal end of needle 400, thus providing a relatively secure connection with the needle. More particularly, the connection between needle holder 1610 and needle 400 is preferably made by inserting the flanged proximal end 460 into internal threaded portion 1612 and then twisting the needle until the flanged area locks into place in the internal threaded portion of the needle holder.

In an embodiment as depicted in FIG. 16, an exterior wall of needle holder 1610 is preferably hexagonal in shape in a lower portion 1620 (which may alternatively be referred to as an extension member of needle holder 1610) and cylindrical in shape in an upper portion 1622, as shown in the isometric view of FIG. 16A, with exception of the proximal end where flange 1611 is located (and the protrusion at the distal end). As shown in FIG. 16, the proximal end immediately above the flange 1611 has a conical shape, by way of illustration but not of limitation (see, for example, the illustration in FIG. 16D, which depicts the exterior shape thereof as being somewhat tapered); as one alternative, the shape may be cylindrical and still engage the threads on 1600 properly. Needle holder 1610 may serve to provide additional strength for the assembly, and thus may reduce the likelihood of a physical failure during use.

Preferably, syringe adapter 1600 and needle holder 1610 are constructed from a plastic or a composite. Syringe adapter 1600 and/or needle holder 1610 may alternatively be constructed from another material, such as stainless steel, aluminum, or another metal (or a combination thereof), without deviating from the scope of the present invention—although as discussed earlier, using a material such as plastic for the syringe adapter and needle holder advantageously allows these components to be recyclable.

Syringe adapter 1600 may optionally be configured as a permanent attachment to (or replacement for) syringe tip 340, rather than being removably affixed thereto. (See the discussion of FIGS. 18-21, below, which depict embodiments that replace a conventional syringe tip.) While not illustrated in FIG. 16, the distal end of the sidewall 1602 of syringe adapter 1600 may be relatively sharp, for ease of inserting this distal end into a bottle of medication (for example), as contrasted to the generally blunt opening that is illustrated for this embodiment in FIG. 16D. (See the discussion of FIGS. 17-19, below, which depict embodiments having a relatively sharp tip—i.e., a tip that is not generally blunt—on the distal end of a syringe adapter.)

Reference number 1619 denotes the opening in the distal end of needle holder 1610. As discussed above with reference to needle holder 1500, the inside diameter of opening 1619 is preferably approximately 0.08 inches, and in an embodiment, the outside diameter conforms to measurements for Luer-type lock connections as stated in International Standard ISO 80369-7:2016 to accommodate a Luer-type lock connection to a needle 400 that is manufactured in conformance with such measurements. Preferably, a length of an inner chamber 1613 of needle holder 1610 extends from the attachment point in support hub member 1601 to cover the distal end of syringe adapter 1600 (as illustrated in the non-exploded cross-sectional view in FIG. 16C). Reference number 1619 denotes the opening at the distal end of needle holder 1610, and it will be understood that the opening at the proximal end of inner chamber 1613 is located at the proximal end of needle holder 1610 (i.e., at the end where flange 1611 is located). Note that while the needle holder 1610 and needle 400 may be removed as a unit from the syringe adapter 1600, this is by way of example; alternatively the needle may be removed from the needle holder and the needle holder may then be removed from the syringe adapter, without deviating from the scope of the present invention.

FIG. 17 illustrates still another embodiment of the disclosed syringe adapter, showing exterior views as well as cross-sectional views of placement thereof upon a syringe and as exploded. The embodiment illustrated in FIG. 17 includes a needle holder to which a needle may be removably affixed. In this embodiment, a needle 400 is removably affixed to a needle holder 1710 that, in turn, is removably affixed to a syringe adapter 1700 that is removably affixed to a syringe 300 for the injection of medication into a recipient. When the injection is completed, the needle 400 preferably remains affixed to the needle holder 1710, enabling needle 400 and needle holder 1710 to be removed from syringe adapter 1700 as a single unit (for example, in preparation for using syringe adapter 1700 for withdrawing additional fluid medication from a container). This enables the combination of needle holder and needle to be quickly and easily re-installed on the syringe adapter, after the syringe adapter is used for withdrawing a next dosage of medication, for administering that next dosage. (It should be noted that the cross-sectional views in FIG. 17 illustrate a preferred interior and exterior shape of components 1700, 1710, but embodiments are not limited to the specific shapes and/or relative dimensions as shown except as otherwise noted herein.)

Figure 17A:
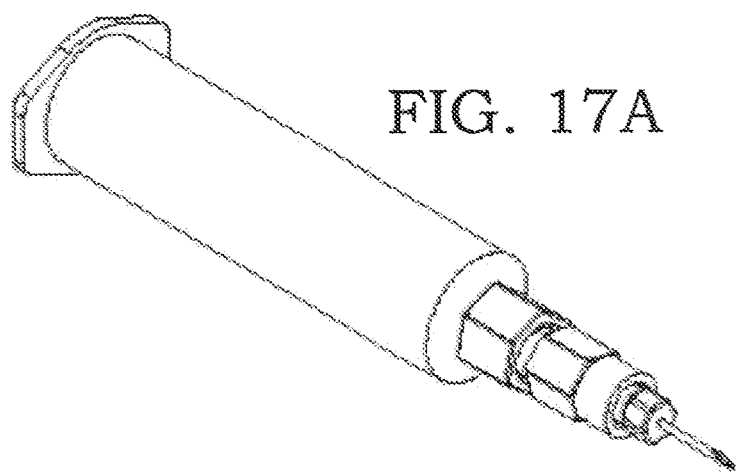
FIG. 17 shows a syringe adapter having a sharp tip and both
Figure 17B:
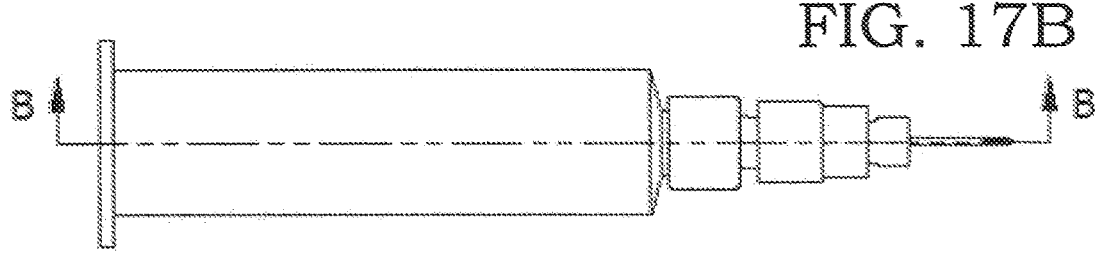
Figure 17C:
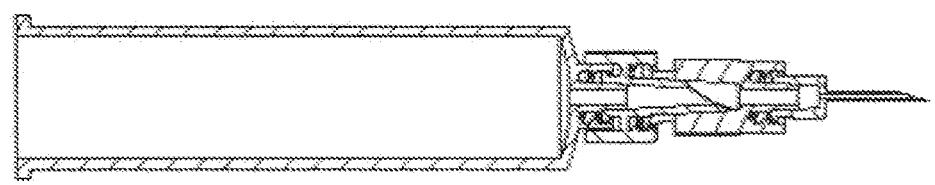
Figure 17D:
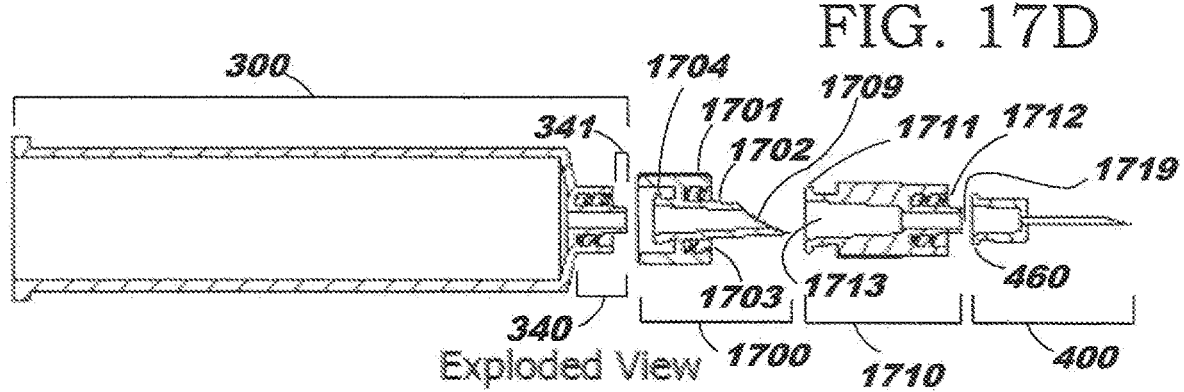

Preferably, syringe adapter 1700 is configured with a support hub member 1701 that radially surrounds at least a portion of the length of the syringe adapter sidewall 1702. In an embodiment as illustrated in FIG. 17, the exterior of the outer wall of support hub member 1701 has a hexagonal shape (as shown in FIG. 17A). This hexagonal shape may enable a person to have a better grasp when connecting or disconnecting the syringe adapter 1700 to syringe 300 and/or needle holder 1710. (Note that while FIG. 17A illustrates the exterior of support hub member 1701 as being hexagonal in shape, this is by way of illustration but not of limitation, and the exterior may be configured to have a different shape without deviating from the scope of the present invention.)

Notably, a tip at the distal end of sidewall 1702 (noting that the distal end of sidewall 1702 is the end at which reference number 1702 is generally located, and reference number 1704 denotes a flanged proximal end of sidewall 1702) is shown in FIG. 17 as having a relatively sharp point. The sharp point, or tip, is designed to assist in inserting the syringe adapter 1700 into the rubber membrane on a medicine bottle. The particular taper illustrated in FIG. 17 for this sharp point may be adjusted, thereby altering the degree of sharpness, without deviating from the scope of the present invention.

A Luer-type lock connection between syringe adapter 1700 and syringe tip 340 is preferably made in the manner discussed above with reference to FIG. 15, and accordingly, details of the connection are not repeated here. A result of the connection is illustrated in the non-exploded cross-sectional view in FIG. 17C.

In an embodiment, the opening 1709 at the distal end of sidewall 1702 (noting that the distal end of sidewall 1702 is the end at which reference number 1702 is generally located) is approximately 0.10 inches in inside diameter (and as discussed in further detail hereinafter, the diameter is preferably about 0.05 inches to about 0.1585 inches, and more preferably, is about 0.078 inches to about 0.14 inches, and even more preferably, is about 0.09 inches to about 0.11 inches, and generally, is approximately 0.10 inches). In the illustration as shown, the distal end of sidewall 1702 extends beyond the distal end of support hub member 1701 (i.e., the end where reference number 1703 is generally located, the proximal end of support hub member 1701 being opposite thereto) to allow the distal end of sidewall 1702 to penetrate the rubber membrane on the medication bottle. Reference number 1704 denotes a flanged proximal end of sidewall 1702.

A distal end of support hub member 1701 is preferably configured with an internal threaded portion, similar to the threaded portion discussed above with reference to support hub member 1501 of FIG. 15, and a Luer-type lock connection between syringe adapter 1700 and needle holder 1710 is preferably made using the threads (illustrated in FIG. 17 generally by small extensions 1703) and the flanged area 1711 (which may alternatively be referred to as a tabbed area) at the proximal end of needle holder 1710 in the manner discussed above with reference to FIG. 15. See the non-exploded cross-sectional view in FIG. 17C.

Needle holder 1710 is configured for removably attaching a needle 400. Needle holder 1710 includes an internal threaded portion (see reference number 1712) on its distal end (i.e., the end where reference number 1712 is generally located), where these threads are configured to provide a Luer-type lock connection with the flange 460 at the proximal end of needle 400, thus providing a relatively secure connection with the needle. More particularly, the connection between needle holder 1710 and needle 400 is preferably made by inserting the flanged proximal end 460 into internal threaded portion 1712 and then twisting the needle until the flanged area locks into place in the internal threaded portion of the needle holder.

In an embodiment as depicted in FIG. 17, an exterior wall of needle holder 1710 is preferably hexagonal in shape in a lower portion and cylindrical in shape in an upper portion, as shown in the isometric view in FIG. 17A, with exception of the proximal end where flange 1711 is located (and the protrusion at the distal end). As shown in FIG. 17, the proximal end immediately above the flange 1711 has a conical shape, by way of illustration but not of limitation (see, for example, the illustration in FIG. 17D, which depicts the exterior shape thereof as being somewhat tapered); as one alternative, the shape may be cylindrical and still engage the threads on 1700 properly. Needle holder 1710 may serve to provide additional strength for the assembly, and thus may reduce the likelihood of a physical failure during use.

Reference number 1719 denotes the opening in the distal end of needle holder 1710. As discussed above with reference to needle holder 1500, the inside diameter of opening 1719 is preferably approximately 0.08 inches, and in an embodiment, the outside diameter conforms to measurements for Luer-type lock connections as stated in International Standard ISO 80369-7:2016 to accommodate a Luer-type lock connection to a needle 400 that is manufactured in conformance with such measurements. As contrasted to the inner chamber 1613 of needle holder 1610, it will be noted that the inner chamber 1713 of needle holder 1710 is approximately twice as long as chamber 1613. This added length serves to accept the full length of the elongated tip 1702 of syringe adapter 1700, as can be seen in the non-exploded cross-sectional view in FIG. 17C, and thus the length of inner chamber 1713 extends from the attachment point in support hub member 1701 to cover the distal end of syringe adapter 1700. Reference number 1719 denotes the opening at the distal end of needle holder 1710.

Preferably, syringe adapter 1700 and needle holder 1710 are constructed from a plastic or a composite. Syringe adapter 1700 and/or needle holder 1710 may alternatively be constructed from another material, such as stainless steel, aluminum, or another metal (or a combination thereof), without deviating from the scope of the present invention—although as discussed earlier, using a material such as plastic for the syringe adapter and needle holder advantageously allows these components to be recyclable.

Syringe adapter 1700 may optionally be configured as a permanent attachment to (or replacement for) syringe tip 340, rather than being removably affixed thereto. (See the discussion of FIGS. 18-21, below, which depict embodiments that replace a conventional syringe tip.)

Note that while the needle holder 1710 and needle 400 may be removed as a unit from the syringe adapter 1700, this is by way of example; alternatively the needle may be removed from the needle holder and the needle holder may then be removed from the syringe adapter, without deviating from the scope of the present invention.

FIGS. 18 and 19 illustrate additional embodiments of the disclosed syringe adapter, showing exterior views as well as cross-sectional views of placement thereof upon a syringe and as exploded. FIGS. 18 and 19 are similar, and thus will be described together. The embodiments illustrated in FIGS. 18 and 19 include a needle holder to which a needle may be removably affixed. In these embodiments, a needle 400 is removably affixed to a needle holder 1810 or 1910 that, in turn, is removably affixed to a syringe adapter 1800 or 1900 that is removably affixed to a syringe 300' for the injection of medication into a recipient. When the injection is completed, the needle 400 preferably remains affixed to the needle holder 1810 or 1910, enabling needle 400 and needle holder 1810 or 1910 to be removed from syringe adapter 1800 or 1900 as a single unit (for example, in preparation for using syringe adapter 1800, 1900 for withdrawing additional fluid medication from a container). This enables the combination of needle holder and needle to be quickly and easily re-installed on the syringe adapter, after the syringe adapter is used for withdrawing a next dosage of medication, for administering that next dosage. (It should be noted that the cross-sectional views in FIGS. 18 and 19 illustrate a preferred interior and exterior shape of components 1800, 1810, 1900, 1910, but embodiments are not limited to the specific shapes and/or relative dimensions as shown except as otherwise noted herein.)

As shown in FIGS. 18 and 19, syringe adapters 1800, 1900 are preferably configured with a support hub member 1801, 1901 that is a solid piece surrounding an inner chamber, in contrast to the approach of the support hub members shown in FIGS. 15-17, with an extension from the proximal end (see 1804, 1904) and an extension from the distal end (see the location of reference numbers 1802, 1902) of this support hub member, where this distal end extension is analogous to previously-discussed distal end of a sidewall. (The proximal end of support hub members 1801, 1901 is the end where reference numbers 1806, 1906 are generally located, and the distal end of the support hub members 1801, 1901 is the end where reference numbers 1803, 1903 are generally located.) In embodiments as illustrated in FIGS. 18 and 19, the exterior of the support hub members 1801, 1901 have a generally hexagonal shape (see FIGS. 18A, 19A), although another shape (such as cylindrical) may be used without deviating from the scope of the present invention.

FIGS. 18 and 19 depict a tip 1802, 1902 extending as a sidewall from the distal end of support hub members 1801, 1901, where these tips are shown as having a relatively sharp point. Reference numbers 1809, 1909 indicate the opening formed by the sidewall at the distal end of syringe adapter 1800, 1900, respectively. In an embodiment, openings 1809, 1909 are each approximately 0.10 inches in inside diameter (and as discussed in further detail hereinafter, the diameter is preferably about 0.05 inches to about 0.1585 inches, and more preferably, is about 0.078 inches to about 0.14 inches, and even more preferably, is about 0.09 inches to about 0.11 inches, and generally, is approximately 0.10 inches). As discussed above, the sharp point is designed to assist in inserting the syringe adapter 1800, 1900 into the rubber membrane on a medicine bottle, and the particular taper may be adjusted from the angle shown in the figures, thereby altering the degree of sharpness, without deviating from the scope of the present invention. (It should also be noted that the sharp point may be eliminated, using instead a tip generally similar to the shape illustrated in FIGS. 15-16, and such alternative shape is deemed to be within the scope of the present invention. See FIGS. 20 and 21, which correspond to FIGS. 18 and 19, respectively, but show an alternative approach where the sharp point is not used. The descriptions of FIGS. 18 and 19 apply equally to the embodiments depicted in FIGS. 20 and 21, except as noted herein.)

FIGS. 18 and 19 also depict a change to how the syringe adapter 1800, 1900 attaches to a syringe. Rather than forming a Luer-type lock connection between syringe adapter 1800, 1900 and a syringe tip such as tip 340, the approach shown in FIGS. 18 and 19 is to remove the syringe tip from the syringe (or equivalently, to use a syringe which has not been fitted with a syringe tip). In a preferred approach, connection between the syringe adapter 1800, 1900 and a syringe is made by inserting an extension 1804, 1904 at the proximal end of the syringe adapter into a cavity 342 where the syringe tip would have been located. Notably, conventional syringe tips are made to be removable in some syringes, allowing for cleaning (for example). Accordingly, threads into which such removable syringe tips are connected may be leveraged for connecting the extensions 1804, 1904. The internal cavity 342 of a typical syringe is configured to provide a female threaded portion, and the proximal end of the syringe adapter 1800, 1900 is thus preferably configured to provide a male connector (such as the previously-discussed flange or tabs) at extensions 1804, 1904. In an embodiment, a Luer-type locking connection is made between cavity 342 and extensions 1804, 1904 by sizing extensions 1804, 1904 to conform to measurements for Luer-type lock connections as stated in International Standard ISO 80369-7:2016, thereby enabling a secure attachment to a cavity 342 that is manufactured in conformance with such measurements. The syringe adapters 1800, 1900 may therefore serve as a permanent attachment to a syringe, or as a replacement for a syringe tip. The syringe adapters 1800, 1900 may alternatively be viewed and/or configured as a semi-permanent attachment or replacement, in that it can be removed if desired. Preferably, syringe adapters 1800, 1900 include a rubber gasket (or similar fitting) on an underside of the support hub member 1801, 1901, as shown by reference numbers 1806, 1906. A result of the connection is illustrated in the non-exploded cross-sectional views in FIGS. 18C and 19C.

Syringe adapters 1800, 1900 differ in the width of extensions 1804, 1904. A corresponding width is used for cavity 342. FIGS. 18 and 19 both illustrate the exterior of support hub members 1801, 1901 as being generally hexagonal in shape, although this is by way of illustration but not of limitation and the exterior may be configured to have a different shape without deviating from the scope of the present invention.

A distal end of support hub members 1801, 1901 is preferably configured with an internal threaded portion, similar to the threaded portion discussed above with reference to support hub member 1501 of FIG. 15, and a Luer-type lock connection between syringe adapter 1800, 1900 and needle holder 1810, 1910 is made using the threads (illustrated in FIGS. 18 and 19 generally by small extensions 1803, 1903) and flanged area 1811, 1911 (which may alternatively be referred to as a tabbed area) at the proximal end of needle holder 1810, 1910 in the manner discussed above with reference to FIG. 15. See the non-exploded cross-sectional views in FIGS. 18C and 19C.

Needle holders 1810, 1910 are configured for removably attaching a needle 400 using a Luer-type lock connection between an internal threaded portion 1812, 1912 on the distal end of the needle holder (i.e., the end where reference numbers 1812, 1912 are generally located) and a flanged area 460 of needle 400 in the manner discussed above with reference to FIGS. 16 and 17, and accordingly, details of the connection are not repeated here. A result of the connection is illustrated in the non-exploded cross-sectional views in FIGS. 18C and 19C.

Figure 18A:
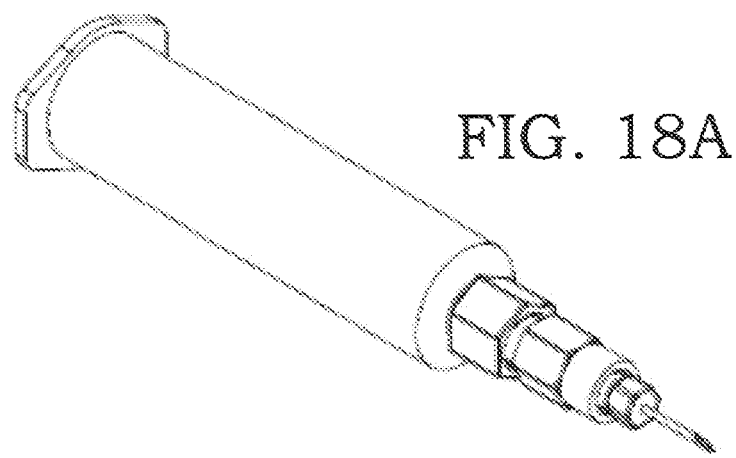
FIGS. 18 (comprising FIGS. 18A through 18D) and 19 (comprising FIGS. 19A through 19D) illustrate embodiments of the disclosed syringe adapter that replace a conventional syringe tip, showing exterior views as well as cross-sectional views of placement thereof upon a syringe and as exploded, and FIGS. 20-21 (comprising FIGS. 20A through 20D and 21A through 21D, respectively) illustrate alternative approaches for a portion of the syringe adapters and needle holders shown in FIGS. 18 and 19.
Figure 18B:
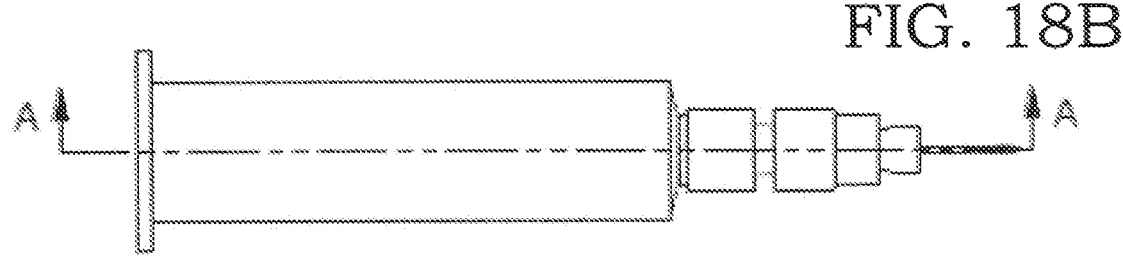
Figure 18C:
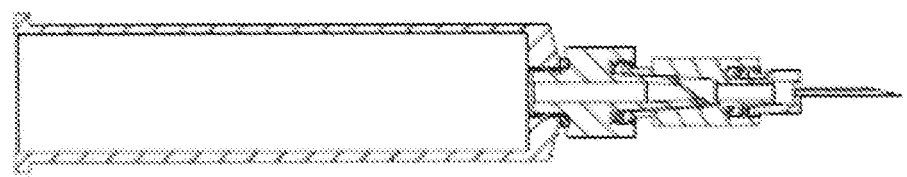
Figure 18D:
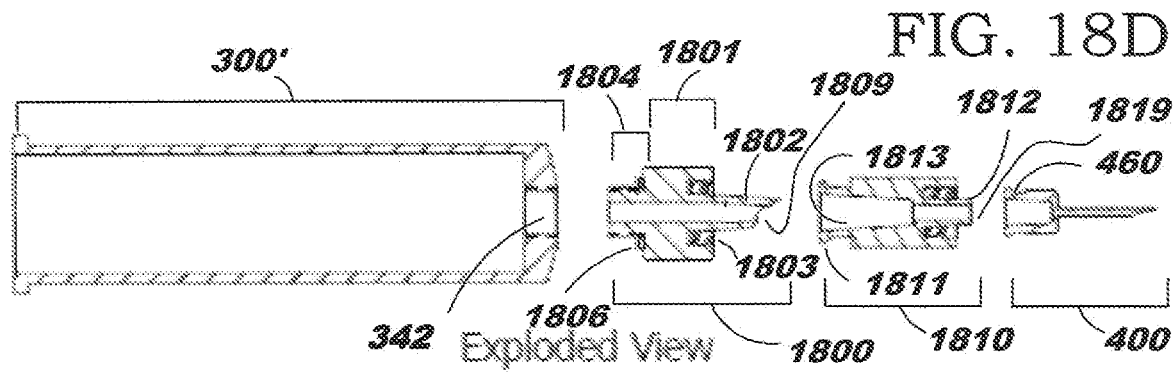
Figure 19A:
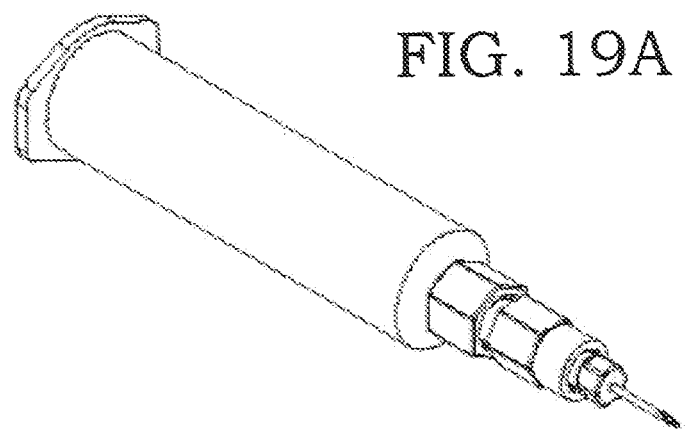
Figure 19B:
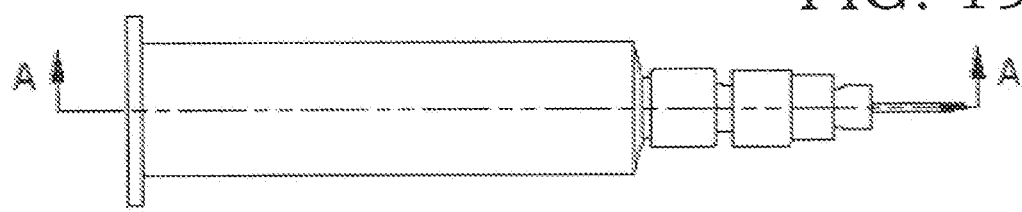
Figure 19C:
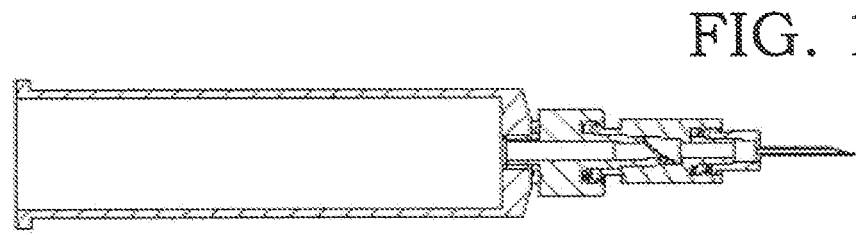
Figure 19D:
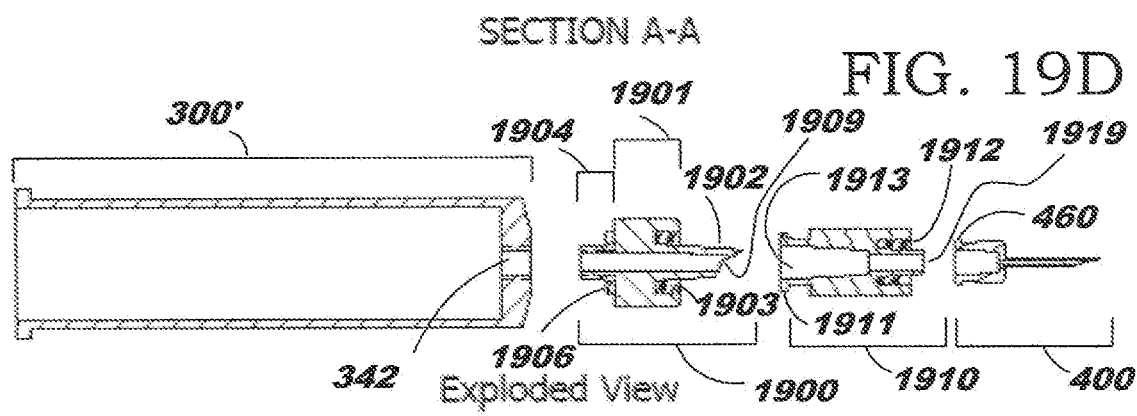
Figure 20A:
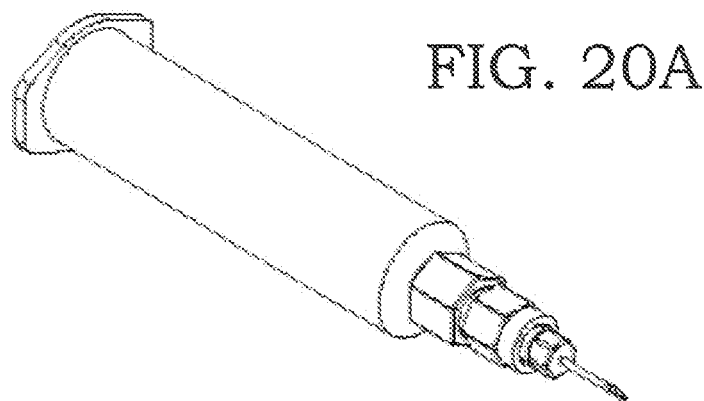
Figure 20B:
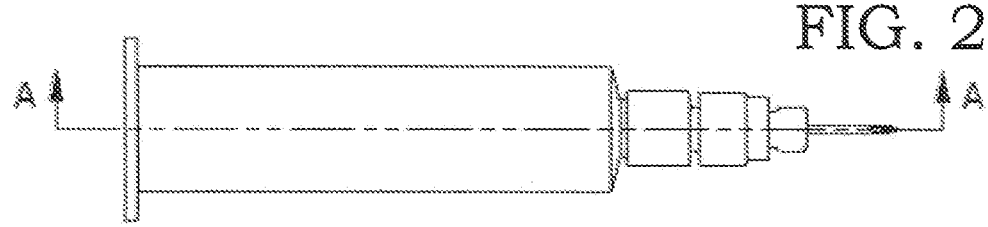
Figure 20C:
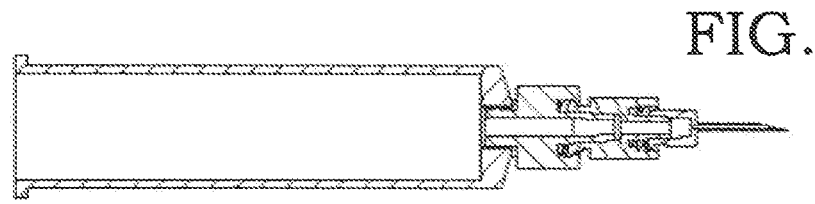
Figure 20D:
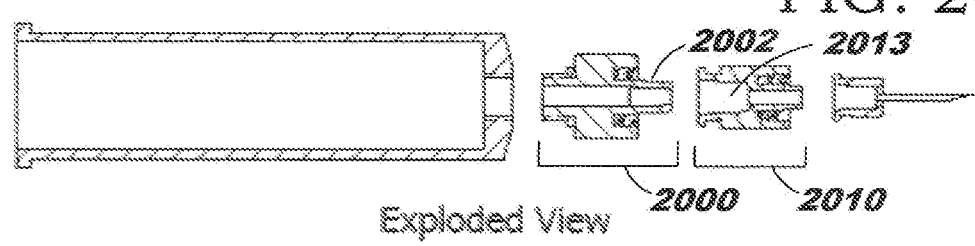
Figure 21A:
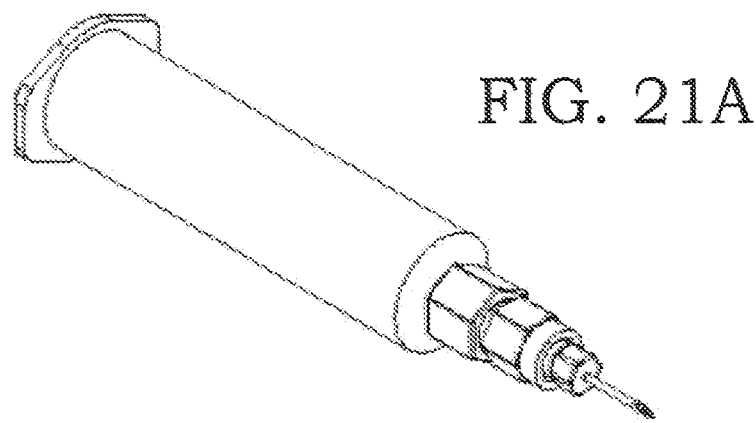
Figure 21B:
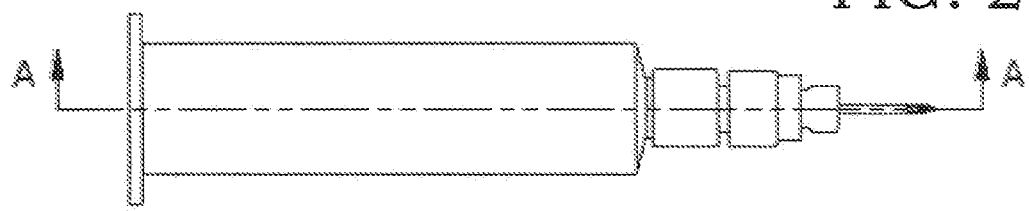
Figure 21C:
Figure 21D:
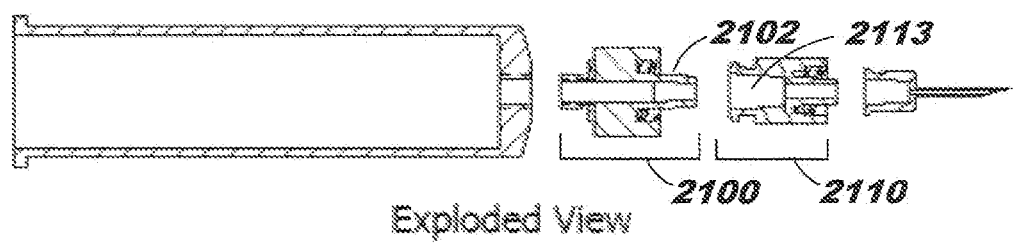

In embodiments as depicted in FIGS. 18 and 19, an exterior wall of needle holders 1810, 1910 is preferably hexagonal in shape in a lower portion and cylindrical in shape in an upper portion, as shown in the isometric views of FIGS. 18A and 19A, with exception of the proximal end where flange 1811, 1911 is located (and the protrusion at the distal end). As shown in FIGS. 18 and 19, the proximal end immediately above the flange 1811, 1911 has a conical shape, by way of illustration but not of limitation (see, for example, the illustrations in FIGS. 18D and 19D, which depict the exterior shape thereof as being somewhat tapered); as one alternative, the shape may be cylindrical and still engage the threads on 1800, 1900 properly. Needle holder 1810, 1910 may serve to provide additional strength for the assembly, and thus may reduce the likelihood of a physical failure during use.

Reference numbers 1819, 1919 denote the opening in the distal end of needle holders 1810, 1910. As discussed above with reference to needle holder 1500, the inside diameter of openings 1819, 1919 is preferably approximately 0.08 inches, and in an embodiment, the outside diameter conforms to measurements for Luer-type lock connections as stated in International Standard ISO 80369-7:2016 to accommodate a Luer-type lock connection to a needle 400 that is manufactured in conformance with such measurements. The length of inner chambers 1813, 1913 of needle holders 1810, 1910 preferably extends from the attachment point in support hub member 1801, 1901 to cover the distal end of syringe adapter 1800, 1900, thus accepting the full length of the elongated tips 1802, 1902 of syringe adapters 1800, 1900, as can be seen in the non-exploded cross-sectional views in FIGS. 18C and 19C. The embodiments depicted in FIGS. 20 and 21 differ from those of FIGS. 18 and 19 primarily because the blunt tips 2002 and 2102 of syringe adapters 2000 and 2100, respectively, are somewhat shorter in length than sharp tips 1802, 1902; accordingly, the inner chambers 2013, 2113 of needle holders 2010, 2110 may be shorter in length than chambers 1813, 1913 while still accepting the full length of tips 2002, 2102 as can be seen in the non-exploded cross-sectional view in FIGS. 20C and 21C.

Preferably, syringe adapters 1800, 1900 and needle holders 1810, 1910 are constructed from a plastic or a composite. Syringe adapters 1800, 1900 and/or needle holders 1810, 1910 may alternatively be constructed from another material, such as stainless steel, aluminum, or another metal (or a combination thereof), without deviating from the scope of the present invention—although as discussed earlier, using a material such as plastic for the syringe adapters and needle holders advantageously allows these components to be recyclable.

Note that while the needle holders 1810, 1910 and needle 400 may be removed as a unit from the syringe adapters 1800, 1900, this is by way of example; alternatively the needle may be removed from the needle holder and the needle holder may then be removed from the syringe adapter, without deviating from the scope of the present invention.

It should be noted that while discussions herein refer primarily to making a locking connection by twisting a first feature within a second feature, it will be obvious that the second feature may be twisted within the first feature or that both features may be twisted, without deviating from the scope of the present invention.

Use of the disclosed syringe adapter while medicating an animal operates, in some embodiments, as follows: the syringe adapter is affixed to a syringe (which, as noted earlier, is preferably a pistol-grip or tab-handled syringe); the syringe adapter is inserted into a bottle of medication; the plunger of the syringe is pulled back to withdraw the desired dosage of medication from the bottle into the syringe barrel; the syringe adapter (which remains attached to the syringe) is removed from the bottle, while the plunger remains stationary; the syringe adapter is replaced with a needle; and the medication (or some portion thereof) is then injected by pushing the plunger forward (for example, by squeezing the pistol-grip handles or pressing down on the tabbed handle) to expel medication from the syringe barrel. If it is desired to reuse the syringe adapter, then the needle is removed from the syringe, after which the above process is repeated. (As noted earlier, the disclosed syringe adapter is not limited to use with medication intended for any particular type of animal life, and therefore the medication may be injected more generally into a "target" or a "recipient".)

Use of the disclosed syringe adapter operates, in some other embodiments, as follows: the syringe adapter is affixed to a syringe (preferably a pistol-grip or tab-handled syringe); the syringe adapter is inserted into a bottle of medication; the plunger of the syringe is pulled back to withdraw the desired dosage of medication from the bottle into the syringe barrel; the syringe adapter (which remains attached to the syringe) is removed from the bottle, while the plunger remains stationary; a needle is affixed to the syringe adapter (and note that the syringe adapter remains affixed to the syringe); and the medication (or some portion thereof) is then injected by pushing the plunger forward (for example, by squeezing the pistol-grip handles or pressing down on the tabbed handle) to expel medication from the syringe barrel. If it is desired to reuse the syringe adapter (for example, for withdrawing additional fluid for medicating another animal), then the needle is removed from the syringe adapter, after which the above process of withdrawing medication using the syringe adapter, affixing a needle thereto, and then injecting the medication (or some portion thereof) is repeated.

Use of the disclosed syringe adapter operates, in still other embodiments, as follows: the syringe adapter is affixed to a syringe (preferably a pistol-grip or tab-handled syringe), and this attachment may be temporary (i.e., removable), permanent, or semi-permanent (that is, intended as a permanent replacement for a conventional syringe tip, although being configured to be removable, such as for cleaning); the syringe adapter is inserted into a bottle of medication; the plunger of the syringe is pulled back to withdraw the desired dosage of medication from the bottle into the syringe barrel; the syringe adapter (which remains attached to the syringe) is removed from the bottle, while the plunger remains stationary; a needle holder, to which a needle is affixed (either before or after connecting the needle holder and the syringe adapter), is affixed to the syringe adapter (and note that the syringe adapter remains affixed to the syringe); and the medication (or some portion thereof) is then injected by pushing the plunger forward (for example, by squeezing the pistol-grip handles or pressing down on the tabbed handle) to expel medication from the syringe barrel. If it is desired to reuse the syringe adapter (for example, for withdrawing additional fluid for medicating another animal), then the needle holder and its affixed needle are removed from the syringe adapter (preferably as a single unit), after which the above process of withdrawing medication using the syringe adapter, affixing a needle holder with needle to the syringe adapter, and then injecting the medication (or some portion thereof) is repeated.

It should be noted that while embodiments are described herein as conforming to the above-cited International Standards and/or as using Luer-type connections to a syringe, this is by way of illustration but not of limitation. It should also be noted that the figures are directed toward illustrating aspects of the present invention, in combination with descriptions herein, and aspects shown therein (for example, length, width, and/or taper) are not necessarily drawn to scale.

While medications have been discussed herein as commonly being sold in a multi-dose bottle, this is by way of illustration and not of limitation. The disclosed syringe adapter may be used beneficially for medication that is sold in a single-use dosage. Also, it should be noted that while some discussions herein refer to expelling "the withdrawn medication" or "emptying" the syringe, this is by way of illustration and not of limitation: the scope of the present invention does not require withdrawn medication to be expelled in full nor does it require a syringe to be fully emptied.

Advantageously, the disclosed syringe adapter may be included with purchase (e.g., within the packaging) of a higher-viscosity medication. As one alternative, a multi-pack of the disclosed syringe adapter may be included with such purchase, particularly when the medication is sold in a multi-dose bottle. The disclosed syringe adapter may also be sold separately from medication. Advantageously, a supplier of packaged syringe adapters may ensure that they are sterilized and/or sanitized by distributing them in sealed packaging.

Examples of higher-viscosity animal medications with which the disclosed syringe adapter may be used beneficially include Nuflor®, Nuflor Gold®, and Resflor Gold®. ("Nuflor", "Nuflor Gold", and "Resflor Gold" are registered trademarks of Intervet Inc. in the United States, other countries, or both. Intervet is now known as "Merck Animal Health".) These medications are commonly sold in 500-milliliter multi-dose bottles and may be administered, by way of example, in dosages of 36 to 60 milliliters per animal. Accordingly, a single multi-dose bottle may be used to treat generally 8 to 14 animals at this dosage range.

As noted earlier, viscosity of a substance may vary with temperature. Viscosity is commonly measured in units termed "centipoise", which may be abbreviated as "cP" or "cps". Water, at 70 degrees Fahrenheit, has a viscosity of approximately 1 cps, and by way of comparison, blood generally has a viscosity of about 10 cps. By convention, a temperature of 70 degrees Fahrenheit is used as a reference point for measuring cps, and thus when a temperature is not mentioned for a particular cps measurement, it should be assumed that the temperature associated with the stated measurement is 70 degrees Fahrenheit.

According to a study documented in "Syringeability and Viscosity Comparative of Different Florfenicol Formulations" by S. Colomer, et al., date unknown, the viscosity of Nuflor® at 5 degrees Celsius (which is approximately 41 degrees Fahrenheit) was 321 cps. U.S. Pat. No. 8,034,845, titled "Compositions and Method for Treating Infection in Cattle and Swine", discusses a formulation believed to correspond to Nuflor Gold® and states that formulations of the invention disclosed therein preferably "have a viscosity of less than about 125 cps".

An embodiment of the present invention is believed to be advantageous for fluid medications having a viscosity of at least 50 to 100 cps at a temperature of at least 5 degrees Celsius, as well as for fluid medications having a higher cps at this temperature (noting, as stated above, that viscosity varies with temperature).

FIG. 22 presents tables containing measurements from tests conducted to compare use of a sample version of the disclosed syringe adapter to use of conventional needles. The tested medication was Resflor Gold®, and a withdrawn quantity thereof was 30 cc (computed as a desired volume for treating an animal with a body weight of 500 pounds). Results of these tests will now be discussed.

In a first test (denoted "Test #1" in FIG. 22), the medication was at room temperature. A withdrawal rate was measured using an 18-gauge needle having a 1-inch length, a 16-gauge needle having a ⅝-inch length, and the syringe adapter. A 16-gauge needle has a larger tip opening (i.e., a larger inside) than an 18-gauge needle, and will therefore withdraw a solution faster than the 18-gauge, although the 16-gauge needle is thought to be disfavored for at least some situations because it may allow the (relatively expensive) medication to leak out of the animal during the medicating process. In addition, a 16-gauge needle is thought to be too large to use on smaller animals. In the sample version, the diameter of the opening in the distal end of the syringe adapter was approximately 0.094 inches.

In this first test, the bottle of medication was placed upon a table and the syringe adapter was already mounted upon a syringe held by the tester, and the elapsed withdrawal times include picking up the bottle and inserting the syringe adapter into the bottle. As shown in FIG. 22, withdrawing 30 cc of Resflor Gold® in this test environment required 3 minutes 50.30 seconds using the 18-gauge needle and 35 seconds using the 16-gauge needle, as compared to 8 seconds using the syringe adapter.

Time to expel the 30 cc of medication was also tested in this first test. Expelling the medication in this test environment required 35 seconds using the 18-gauge needle and 11 seconds using the 16-gauge needle. (Time to expel the medication was not measured using the syringe adapter, because the expel time depends on the needle used for injecting the medication.)

In a second test (denoted "Test #2" in FIG. 22), the medication was again at room temperature, but the bottle of medication was now held by the tester to eliminate time required to pick up the bottle. Accordingly, the elapsed withdrawal times in this test begin with inserting the syringe adapter into the bottle. As shown in FIG. 22, withdrawing 30 cc of Resflor Gold® in this test environment required an average of 5.54 seconds when using the syringe adapter, where this average was computed by taking measurements 6 times and discarding a time that appeared to be an outlier. (Because slightly more than 2 seconds were gained by omitting the "pick up" time of the bottle, this test was not performed using the needles: it may be assumed that the withdrawal times using needles in the first test would be approximately 2 seconds less under the environment of this second test.)

In a third test (denoted "Test #3" in FIG. 22), the medication was now at a temperature of approximately 38 to 40 degrees Fahrenheit, having just been removed from refrigeration (noting that this temperature was intended to simulate a cold weather environment in which the tested medication might be used). The bottle of medication and syringe with affixed syringe adapter were again held by the tester (and the elapsed times began with inserting the syringe adapter into the bottle), as in the second test. As shown in FIG. 22, withdrawing 30 cc of the now-cooler-temperature Resflor Gold® in this test environment required 3 minutes 42.27 seconds using the 16-gauge needle, as compared to 1 minute 1 second using the syringe adapter. Note that this third test was not conducted using the smaller 18-gauge needle, but by comparison to the results of the first test, it can be seen that the withdrawal time using the smaller (i.e., 18-gauge) needle may be expected to greatly exceed the nearly 4-minute withdrawal time for the 16-gauge needle.

While a preferred diameter for the hole, or opening, in the distal end of the syringe adapter is about 0.10 inches, embodiments disclosed herein are not limited to this preferred diameter, as noted earlier. Instead, a syringe adapter as disclosed herein may have an opening, or distal end hole, within any suitable range. In addition to the tests discussed above with reference to FIG. 22, which were conducted using a sample version of the syringe adapter in which the distal end opening measured approximately 0.094 inches, additional experiments and testing have been performed using syringe adapter prototypes with a range of sizes for the distal end opening of the syringe adapter, in view of both draw time and impact upon the rubber membrane, and those results will now be discussed.

When considering an upper bound on the size of the opening in the distal end of the syringe adapter, it will be readily understood that throughput time of a fluid drawn into a syringe is necessarily limited by the size of the opening into the syringe itself (that is, the opening at the distal end of the syringe). It is believed that commercially-available syringes adhere to a standardized maximum outer diameter for the tip of a syringe, where this standardized maximum outer diameter is stated in a version of the above-cited International Standards as about 0.1585 inches. The version of the International Standards did not appear to state a standardized inner diameter for the tip of a syringe, and accordingly, the measurement of 0.1585 inches has been adopted for preferred embodiments because it is deemed to necessarily provide an upper bound on the inner diameter of the syringe tip and therefore on the width of the opening through which fluid will enter the syringe. It is noted that commercially-available syringes have distal end openings in different inner diameters. Several commercially-available syringes were measured, and were found to have distal end openings that range from an inner diameter of 0.0625 inches to 0.1094 inches, for example. In view of this information, it is noted that the draw time when using a syringe adapter will not be appreciably improved by increasing the syringe adapter distal end opening size beyond the limiting size of the opening into the syringe itself. Accordingly, for a syringe having an opening with a maximum inner diameter of about 0.1585 inches, a measurement of about 0.1585 inches forms a de facto upper bound on the size of the distal end opening of the disclosed syringe adapter. In the more general case where the distal end opening of a syringe is smaller or larger than 0.1585 inches, an inner diameter of the distal end opening in the syringe adapter preferably provides compatibility with the size of an inner diameter of the distal end opening into such syringe. Advantageously, using a syringe adapter distal end opening with an inner diameter on the order of the 0.1 inch measurement previously noted herein provides compatibility with a plurality of different syringe opening sizes.

It is noted that a standard opening size for the 16-gauge needle used in the testing of FIG. 22 is about 0.047 inches, and that the above discussion of FIG. 9 referred to an example where the diameter of the distal end of conical portion 940 is approximately 0.156 inches (and when using a sidewall thickness of 0.05 inches, an inner diameter of approximately 0.056 inches). Additional experiments and testing used prototypes with additional opening sizes at the distal end of the syringe adapter to validate earlier conclusions. Draw times using conditions analogous to Test #1 of FIG. 22 were measured for syringe adapter prototypes having distal end inner diameters in increments of 1/64 inch, from decimal measurements of 0.0625 inches through 0.171875 inches (corresponding to 4/64 inches through 11/64 inches), as well as a prototype having a 0.09 inch distal end inner diameter. The average draw time for the prototype with a 0.0625 inch inner diameter was 19.67 seconds. While this is notably improved over the results of the 18-gauge and 16-gauge needles of Test #1, it is significantly less attractive than the average draw time noted for the prototype having the 0.09 inch inner diameter, which had an average draw time of 5.88 seconds. The prototype having a distal end inner diameter of 0.078125 inches yielded an average draw time of 8.45 seconds, showing very significant improvement over the next-smaller 0.0625 inch opening. All remaining prototype sizes in this testing (ranging from 0.09375 inches to 0.17185 inches) showed an average draw time within 0.5 seconds of the prototype with the 0.09 inch inner diameter—notably leveling off in draw time improvement, in spite of increasing the distal end inner diameter, to a variance that will not be detectable by a user. (For example, the average draw times for the prototypes with distal end inner diameters of 0.14 inches and 0.15625 inches were 5.82 seconds and 5.81 seconds, respectively, while the average time for the inner diameter of 0.109 inches was 6.11 seconds.) In view of this information, a preferred inner diameter of the distal end opening in the syringe adapter is in the range of about 0.05 inches to about the maximum size of the distal end opening into the syringe (believed to be about 0.1585 inches, as noted above), and more preferably, this inner diameter is about 0.078 inches to about 0.14 inches, and even more preferably, is about 0.09 inches to about 0.11 inches, and generally, is about 0.10 inches.

A consideration for the outer diameter of the distal end of the syringe adapter is the impact of inserting the distal end of the syringe adapter into the rubber membrane affixed to the top of the bottle. It is noted that some vendors state (for example, in a label affixed to a medicine bottle or perhaps in its accompanying literature) an upper limit on the number of times the rubber membrane can safely be punctured. An example is commercially known, for example, in which the label states that the rubber membrane should not be punctured more than 20 times. This limit is believed to be due to a potentially compromising effect that the puncturing tip of a sharp needle may have on the rubber membrane (where, for example, compromising the rubber membrane may enable the fluid medication to leak out). In view of this consideration, experimentation and testing was performed using prototypes with different sizes for the outer diameter of the distal end of the syringe adapter to determine what outer diameter size might compromise the rubber membrane. In this testing, the distal end of each tested prototype syringe adapter was cylindrical in shape.

For the testing of rubber membrane compromise, it was noted above that a common diameter of the rubber membrane fitted in the top of 250 ml bottles and 500 ml bottles is 0.75 inches. The typical rubber membrane has a dimple in the center where it is intended for the rubber membrane to be penetrated. A common size of this dimple is about 0.1730 inches to about 0.1760 inches. In view of this 0.75 inch membrane size and approximately 0.1750 inch dimple size, an initial test was conducted with a syringe adapter prototype having an outer diameter of approximately 0.26 inches on the distal end. Inserting this prototype through the rubber membrane was extremely difficult, and appeared to compromise the rubber membrane. Accordingly, no further testing above this 0.26 inch outer diameter was deemed beneficial. Another prototype syringe adapter was tested, this time having an outer diameter of 0.1815 inches on the distal end. Inserting this prototype into the rubber membrane was possible with less effort, and did not appear to compromise the rubber membrane. In view of these results, an upper bound on the outer diameter of the distal end of the syringe adapter is preferably about 0.1815 inches for a rubber membrane sized at about 0.75 inches and a corresponding dimple of about 0.1750 inches. In a more general case, an upper bound on the outer diameter of the distal end of the syringe adapter is approximately about the size of the dimple of the rubber membrane.

As has been demonstrated, an embodiment of the present invention improves syringeability of higher-viscosity medications, allowing such medication to be withdrawn from a bottle in much less time as compared to the known approach of withdrawal using a needle. More animals may therefore be medicated in a given period of time, leading to improved productivity of persons caring for the animals as well as enabling overall improved health for the animals. No longer will higher viscosity be a barrier to the market, and because medication of this type will be more readily administered when using a syringe adapter as disclosed herein, improvement may be expected in animal health, and market share and/or market presence for the medication may improve as well.

It should be noted that various features discussed herein with reference to "an embodiment", "one embodiment", "a preferred embodiment", and so forth should not be construed as suggesting that each such feature is present in a single embodiment, or in every embodiment, of the present invention. Instead, it should be understood that there may be various combinations of the disclosed features present in any particular embodiment.

While embodiments of the present invention have been described, additional variations and modifications in those embodiments may occur to those of ordinary skill in the art once they learn of the basic inventive concepts. Therefore, it is intended that the appended claims shall be construed to include the described embodiments and all such variations and modifications as fall within the spirit and scope of the invention.

The invention claimed is:

1. A syringe adapter for withdrawing viscous fluid medication from a container, comprising:
a support hub member radially surrounding an inner chamber, the syringe adapter further comprising an extension from a proximal end of the support hub member and a sidewall extending from a distal end of the support hub member, the distal end of the support hub member being opposite the proximal end of the support hub member, the inner chamber extending through the sidewall and the extension, a terminal edge of a distal end of the sidewall defining a first opening into the inner chamber and a terminal edge of a proximal end of the extension defining a second opening into the inner chamber, wherein:
a proximal end of the syringe adapter connects to a distal end of a syringe by inserting, into a cavity at the distal end of the syringe, the extension from the proximal end of the support hub member, wherein the cavity defines a third opening into the syringe;
a viscous fluid communication path extends through the inner chamber, between the first opening and the second opening;
the first opening provides an entry into the viscous fluid communication path for viscous fluid medication to enter from a container into the inner chamber;
the second opening provides an exit from the viscous fluid communication path for the viscous fluid medication to exit from the inner chamber, through the third opening, into a barrel of the syringe;
the first opening has an inner diameter of at least 0.05 inches; and
the distal end of the support hub member is configured to removably receive a proximal end of a needle holder, the needle holder further comprising a distal end opposite the proximal end of the needle holder, the distal end of the needle holder configured to removably affix thereto a needle.

2. The syringe adapter according to claim 1, wherein the distal end of the support hub member removably receives the proximal end of the needle holder by inserting a flanged area at the proximal end of the needle holder into an internal threaded portion at the distal end of the support hub member.

3. The syringe adapter according to claim 1, wherein the needle is removably affixed to the distal end of the needle holder by inserting a flanged area at a proximal end of the needle into an internal threaded portion at the distal end of the needle holder.

4. The syringe adapter according to claim 1, wherein the proximal end of the syringe adapter is connected to the distal end of the syringe by a permanent attachment between the extension and the cavity.

5. The syringe adapter according to claim 1, wherein the proximal end of the syringe adapter is connected to the distal end of the syringe by a threadable attachment between the extension and the cavity.

6. The syringe adapter according to claim 1, wherein at least a portion of the support hub member is multi-sided in exterior shape.

7. The syringe adapter according to claim 1, wherein the inner diameter is between 0.078 inches and 0.14 inches.

8. The syringe adapter according to claim 1, wherein the inner diameter is at least 0.094 inches.

9. The syringe adapter according to claim 1, wherein the distal end of the sidewall is frustoconical in exterior shape and an interior surface of the distal end of the sidewall defines a distal end of the inner chamber as being frustoconical.

10. An apparatus for withdrawing and administering viscous fluid medication, comprising:
a syringe adapter; and
a needle holder, wherein:
the syringe adapter comprises a support hub member radially surrounding an inner chamber, the syringe adapter further comprising an extension from a proximal end of the support hub member and a sidewall extending from a distal end of the support hub member, the distal end of the support hub member being opposite the proximal end of the support hub member, the inner chamber extending through the sidewall and the extension, a terminal edge of a distal end of the sidewall defining a first opening into the inner chamber and a terminal edge of a proximal end of the extension defining a second opening into the inner chamber;
the proximal end of the extension connects the syringe adapter to a cavity in a distal end of a syringe;
a viscous fluid communication path extends through the inner chamber, between the first opening and the second opening;
the first opening has an inner diameter of at least 0.05 inches;
the needle holder comprises a needle holder sidewall extending between a distal end thereof and a proximal end opposite thereto, the needle holder sidewall having an interior surface defining an interior chamber, the distal end of the needle holder sidewall terminating at a first needle holder opening and the proximal end of the needle holder sidewall terminating at a second needle holder opening, the interior chamber providing a fluid communication path through the needle holder, between the first needle holder opening and the second needle holder opening;
the first opening provides a distal end entry into the viscous fluid communication path for viscous fluid medication to enter from a container into the inner chamber and also provides a distal end exit from the viscous fluid communication path for the viscous fluid medication to exit from the inner chamber, through the second needle holder opening and into the interior chamber of the needle holder;
the second opening provides a proximal end exit from the viscous fluid communication path for the viscous fluid medication to exit from the inner chamber, through a third opening defined by the cavity and into a barrel of the syringe and also provides a proximal end entry into the viscous fluid communication path for the viscous fluid medication to exit from the barrel, through the third opening and the second opening and into the inner chamber;
a flanged area extends outwardly from a terminal edge of the proximal end of the needle holder sidewall;
the needle holder further comprises a wall radially surrounding at least a portion of an exterior surface of the distal end of the needle holder sidewall, at least a portion of an inner surface of the wall configured with an internal threaded area for threadably connecting thereto a proximal end of a needle; and
a distal end of the support hub member, located opposite the proximal end of the support hub member, is configured with an internal threaded portion for threadably receiving the flanged area extending outwardly from the terminal edge of the proximal end of the needle holder sidewall.

11. The apparatus according to claim 10, wherein:
a flanged area extends outwardly from the terminal edge of the proximal end of the extension; and
the connection of the syringe adapter to the cavity is a threadable connection whereby the flanged area threadably connects to an internal threaded portion of the cavity.

12. The apparatus according to claim 10, wherein the connection of the syringe adapter to the cavity is a permanent connection.

13. The apparatus according to claim 10, wherein the inner diameter is between 0.078 inches and 0.14 inches.

14. The apparatus according to claim 10, wherein the inner diameter is at least 0.094 inches.

15. The apparatus according to claim 10, wherein the distal end of the sidewall is frustoconical in exterior shape and an interior surface of the distal end of the sidewall defines a distal end of the inner chamber as being frustoconical.

16. A system for administering viscous fluid medication withdrawn from a container into a syringe, comprising:
a syringe, the syringe having a distal end and an opposite proximal end and configured with a barrel extending between the distal end and the proximal end, the distal end configured with a cavity to receive a syringe tip formed as a needle-attachment point, the cavity defining an opening into the barrel;
a needle;
a syringe adapter configured for connecting to the syringe, the syringe adapter comprising a support hub member radially surrounding an inner chamber, the syringe adapter further comprising an extension from a proximal end of the support hub member and a sidewall extending from a distal end of the support hub member, the distal end of the support hub member being opposite the proximal end of the support hub member, the inner chamber extending through the sidewall and the extension, a terminal edge of a distal end of the sidewall defining a first opening into the inner chamber and a terminal edge of a proximal end of the extension defining a second opening into the inner chamber, wherein:
the syringe adapter connects to the syringe by inserting the extension into the cavity, thereby causing the second opening to provide for fluid communication with the barrel through the opening defined by the cavity;
the distal end of the sidewall is configured for inserting into a container of viscous fluid medication, thereby causing the first opening to be in fluid communication with the viscous fluid medication; and
the syringe adapter is configured to remain connected to the syringe while a drawing mechanism of the syringe is activated to withdraw, from the container, at least a portion of the viscous fluid medication through the first opening and into the inner chamber, and from the inner chamber through the second opening and the opening defined by the cavity and into the barrel of the syringe, wherein the first opening has an inner diameter of between 0.078 inches and 0.14 inches, the viscous fluid medication having a viscosity of at least 50 centipoise units at a temperature of at least 5 degrees Celsius; and a needle holder, the needle holder comprising a proximal end and a distal end opposite thereto, the proximal end of the needle holder configured for threadably affixing to a distal end of the support hub member, subsequent to the withdrawing from the container, by connecting a flanged area at the proximal end of the needle holder to an internal threaded portion in the distal end of the support hub member, a distal end of the needle holder configured for threadably affixing thereto a proximal end of the needle, wherein:

the system is configured for holding the needle threadably affixed to the distal end of the needle holder, while the proximal end of the needle holder remains threadably affixed to the distal end of the support hub member and while the proximal end of the extension of the syringe adapter remains connected to the syringe, and while at least a portion of the viscous fluid medication withdrawn into the barrel is injected from the needle into a recipient.

17. The system according to claim 16, wherein:
a flanged area extends laterally from the terminal edge of the proximal end of the extension; and
the connection of the syringe adapter to the cavity is a threadable connection whereby the flanged area threadably connects to an internal threaded portion of the cavity.

18. The system according to claim 16, wherein the connection of the syringe adapter to the cavity is a permanent connection.

19. The system according to claim 16, wherein the inner diameter is at least 0.094 inches.

20. The system according to claim 16, wherein the distal end of the sidewall is frustoconical in exterior shape and an interior surface of the distal end of the sidewall defines a distal end of the inner chamber as being frustoconical.

\* \* \* \* \*